(12) United States Patent
Ahrens et al.

(10) Patent No.: US 8,092,536 B2
(45) Date of Patent: Jan. 10, 2012

(54) RETENTION STRUCTURE FOR IN SITU FORMATION OF AN INTERVERTEBRAL PROSTHESIS

(75) Inventors: Michael Ahrens, Neustadt i.H. (DE); Erik O. Martz, Savage, MN (US)

(73) Assignee: Disc Dynamics, Inc., Eden Prairie, MN (US)

( * ) Notice: Subject to any disclaimer, the term of this patent is extended or adjusted under 35 U.S.C. 154(b) by 177 days.

(21) Appl. No.: 12/203,727

(22) Filed: Sep. 3, 2008

(65) Prior Publication Data
US 2009/0012618 A1    Jan. 8, 2009

Related U.S. Application Data

(63) Continuation-in-part of application No. 11/420,055, filed on May 24, 2006.

(51) Int. Cl.
*A61F 2/44* (2006.01)
(52) U.S. Cl. .................................................. 623/17.11
(58) Field of Classification Search .... 623/17.11–17.16; 606/200
See application file for complete search history.

(56) References Cited

U.S. PATENT DOCUMENTS

| | | | |
|---|---|---|---|
| 4,545,374 A | 10/1985 | Jacobson | |
| 4,759,766 A * | 7/1988 | Buettner-Janz et al. | ... 623/17.15 |
| 4,834,757 A | 5/1989 | Brantigan | |
| 4,969,888 A | 11/1990 | Scholten et al. | |
| 5,047,055 A | 9/1991 | Bao et al. | |
| 5,171,281 A | 12/1992 | Parsons et al. | |
| 5,269,797 A | 12/1993 | Bonati et al. | |
| 5,285,795 A | 2/1994 | Ryan et al. | |
| 5,314,432 A | 5/1994 | Paul | |
| 5,331,975 A | 7/1994 | Bonutti | |
| 5,395,317 A | 3/1995 | Kambin | |
| 5,413,576 A | 5/1995 | Rivard | |
| 5,425,772 A | 6/1995 | Brantigan | |
| 5,472,426 A | 12/1995 | Bonati et al. | |
| 5,476,473 A | 12/1995 | Heckele | |
| 5,520,678 A | 5/1996 | Heckele et al. | |
| 5,527,312 A | 6/1996 | Ray | |
| 5,556,429 A | 9/1996 | Felt | |

(Continued)

OTHER PUBLICATIONS

Office Action issued in U.S. Appl. No. 11/420,055 dated Dec. 22, 2008.

(Continued)

*Primary Examiner* — Thomas C. Barrett
*Assistant Examiner* — David Bates
(74) *Attorney, Agent, or Firm* — Stoel Rives LLP

(57) ABSTRACT

An assembly for the in situ formation of a prosthesis in an intervertebral disc space between adjacent vertebrae of a patient. At least one retention structure is located in the intervertebral disc space. A distal end of at least one lumen is located proximate the at least one retention structure. One or more in situ curable biomaterials are delivered to the intervertebral disc space through the first lumen and into engagement with the retention structure. The retention structure serves to retain at least a portion of the biomaterial in the intervertebral disc space by surface tension, adhesion, mechanical capture, friction, viscosity, and/or a variety of other mechanisms. The at least partially cured biomaterial and the at least one retention structure cooperate to comprise the prosthesis.

28 Claims, 20 Drawing Sheets

U.S. PATENT DOCUMENTS

| | | |
|---|---|---|
| 5,562,699 A | 10/1996 | Heimberger et al. |
| 5,562,736 A | 10/1996 | Ray et al. |
| 5,584,855 A | 12/1996 | Onik |
| 5,591,227 A | 1/1997 | Dinh et al. |
| 5,599,279 A | 2/1997 | Slotman et al. |
| 5,620,458 A | 4/1997 | Green et al. |
| 5,645,597 A | 7/1997 | Krapiva |
| 5,697,889 A | 12/1997 | Slotman et al. |
| 5,752,969 A | 5/1998 | Cunci et al. |
| 5,762,629 A | 6/1998 | Kambin |
| 5,785,647 A | 7/1998 | Tompkins et al. |
| 5,792,044 A | 8/1998 | Foley et al. |
| 5,795,353 A | 8/1998 | Felt |
| 5,797,909 A | 8/1998 | Michelson |
| 5,800,549 A | 9/1998 | Bao et al. |
| 5,851,214 A | 12/1998 | Larsen et al. |
| 5,888,190 A | 3/1999 | Meyer et al. |
| 5,888,220 A | 3/1999 | Felt et al. |
| 5,902,231 A | 5/1999 | Foley et al. |
| 5,954,635 A | 9/1999 | Foley et al. |
| 5,980,504 A | 11/1999 | Sharkey et al. |
| 6,007,487 A | 12/1999 | Foley et al. |
| 6,022,376 A | 2/2000 | Assell et al. |
| 6,059,325 A | 5/2000 | Heckele et al. |
| 6,063,096 A | 5/2000 | Boebel et al. |
| 6,079,868 A | 6/2000 | Rydell |
| 6,080,155 A | 6/2000 | Michelson |
| 6,096,038 A | 8/2000 | Michelson |
| 6,099,514 A | 8/2000 | Sharkey et al. |
| 6,110,210 A | 8/2000 | Norton et al. |
| 6,140,452 A | 10/2000 | Felt et al. |
| 6,146,420 A | 11/2000 | McKay |
| 6,152,871 A | 11/2000 | Foley et al. |
| 6,162,170 A | 12/2000 | Foley et al. |
| 6,171,236 B1 | 1/2001 | Bonutti |
| 6,187,048 B1 | 2/2001 | Milner et al. |
| 6,206,822 B1 | 3/2001 | Foley et al. |
| 6,217,509 B1 | 4/2001 | Foley et al. |
| 6,224,599 B1 | 5/2001 | Baynham et al. |
| 6,224,630 B1 | 5/2001 | Bao et al. |
| 6,231,609 B1 | 5/2001 | Mehdizadeh |
| 6,235,043 B1 | 5/2001 | Reiley et al. |
| 6,245,107 B1 | 6/2001 | Ferree |
| 6,248,110 B1 | 6/2001 | Reiley et al. |
| 6,270,498 B1 | 8/2001 | Michelson |
| 6,283,966 B1 | 9/2001 | Houfburg |
| 6,306,117 B1 | 10/2001 | Uber, III |
| 6,306,177 B1 | 10/2001 | Felt et al. |
| 6,332,894 B1 | 12/2001 | Stalcup et al. |
| 6,371,990 B1 | 4/2002 | Ferree |
| 6,395,034 B1 | 5/2002 | Suddaby |
| 6,402,750 B1 | 6/2002 | Atkinson et al. |
| 6,402,784 B1 | 6/2002 | Wardlaw |
| 6,419,704 B1 | 7/2002 | Ferree |
| 6,423,083 B2 | 7/2002 | Reiley et al. |
| 6,425,859 B1 | 7/2002 | Foley et al. |
| 6,425,919 B1 | 7/2002 | Lambrecht |
| 6,428,131 B1 | 8/2002 | Fujii et al. |
| 6,428,576 B1 | 8/2002 | Haldimann |
| 6,432,107 B1 | 8/2002 | Ferree |
| 6,436,119 B1 | 8/2002 | Erb et al. |
| 6,443,988 B2 | 9/2002 | Felt et al. |
| 6,458,077 B1 | 10/2002 | Boebel |
| 6,482,219 B1 | 11/2002 | Bonnet |
| 6,482,235 B1 | 11/2002 | Lambrecht et al. |
| 6,491,724 B1 * | 12/2002 | Ferree ................ 623/17.11 |
| 6,508,839 B1 | 1/2003 | Lambrecht et al. |
| 6,520,907 B1 | 2/2003 | Foley et al. |
| 6,520,992 B1 | 2/2003 | Zollner et al. |
| 6,533,799 B1 | 3/2003 | Bouchier |
| 6,558,390 B2 | 5/2003 | Cragg |
| 6,562,072 B1 | 5/2003 | Fuss et al. |
| 6,565,587 B1 | 5/2003 | Heckele et al. |
| 6,579,291 B1 | 6/2003 | Keith et al. |
| 6,582,467 B1 * | 6/2003 | Teitelbaum et al. ....... 623/17.11 |
| 6,592,625 B2 | 7/2003 | Cauthen |
| 6,595,998 B2 | 7/2003 | Johnson et al. |
| 6,599,291 B1 | 7/2003 | Foley et al. |
| 6,607,558 B2 | 8/2003 | Kuras |
| 6,645,248 B2 * | 11/2003 | Casutt ................ 623/17.12 |
| 6,648,895 B2 | 11/2003 | Burkus et al. |
| 6,656,178 B1 | 12/2003 | Veldhuizen et al. |
| 6,663,647 B2 * | 12/2003 | Reiley et al. ................ 606/192 |
| 6,685,695 B2 | 2/2004 | Ferree |
| 6,685,726 B2 | 2/2004 | Black et al. |
| 6,689,125 B1 | 2/2004 | Keith et al. |
| 6,692,501 B2 | 2/2004 | Michelson |
| 6,695,882 B2 | 2/2004 | Bianchi et al. |
| 6,699,294 B2 | 3/2004 | Urry |
| 6,712,853 B2 | 3/2004 | Kuslich |
| 6,719,797 B1 | 4/2004 | Ferree |
| 6,723,058 B2 | 4/2004 | Li |
| 6,726,720 B2 | 4/2004 | Ross et al. |
| 6,733,534 B2 | 5/2004 | Sherman |
| 6,736,835 B2 | 5/2004 | Pellegrino et al. |
| 6,743,255 B2 | 6/2004 | Ferree |
| 6,758,863 B2 | 7/2004 | Estes et al. |
| 6,764,514 B1 | 7/2004 | Li et al. |
| 6,770,074 B2 | 8/2004 | Michelson |
| 6,793,676 B2 | 9/2004 | Plouhar et al. |
| 6,793,677 B2 | 9/2004 | Ferree |
| 6,805,715 B2 | 10/2004 | Reuter et al. |
| 6,824,565 B2 | 11/2004 | Muhanna et al. |
| 6,830,570 B1 | 12/2004 | Frey et al. |
| 6,835,205 B2 | 12/2004 | Atkinson et al. |
| 6,837,892 B2 | 1/2005 | Shoham |
| 6,851,430 B2 | 2/2005 | Tsou |
| 6,852,127 B2 | 2/2005 | Varga et al. |
| 6,875,213 B2 | 4/2005 | Michelson |
| 6,899,716 B2 | 5/2005 | Cragg |
| 6,899,719 B2 | 5/2005 | Reiley et al. |
| 6,921,532 B1 | 7/2005 | Austin et al. |
| 6,932,843 B2 | 8/2005 | Smith et al. |
| 6,936,070 B1 | 8/2005 | Muhanna |
| 6,958,077 B2 | 10/2005 | Suddaby |
| 6,969,404 B2 * | 11/2005 | Ferree ................ 623/17.11 |
| 6,969,405 B2 | 11/2005 | Suddaby |
| 6,983,546 B2 | 1/2006 | Li |
| 6,984,247 B2 | 1/2006 | Cauthen |
| 6,986,772 B2 | 1/2006 | Michelson |
| 7,001,431 B2 | 2/2006 | Bao et al. |
| 7,004,945 B2 | 2/2006 | Boyd et al. |
| 7,004,971 B2 | 2/2006 | Serhan et al. |
| 7,014,633 B2 | 3/2006 | Cragg |
| 7,048,963 B2 | 5/2006 | Braithwaite et al. |
| 7,052,516 B2 | 5/2006 | Cauthen, III et al. |
| 7,056,345 B2 | 6/2006 | Kuslich |
| 7,060,073 B2 | 6/2006 | Frey et al. |
| 7,060,097 B2 | 6/2006 | Fraser et al. |
| 7,077,865 B2 | 7/2006 | Bao et al. |
| 7,083,639 B2 | 8/2006 | Guinan et al. |
| 7,094,258 B2 | 8/2006 | Lambrecht et al. |
| 7,128,746 B2 | 10/2006 | Singer et al. |
| 7,217,273 B2 | 5/2007 | Bonutti |
| 7,534,268 B2 | 5/2009 | Hudgins et al. |
| 7,744,651 B2 * | 6/2010 | Trieu et al. ................ 623/17.16 |
| 2003/0220649 A1 | 11/2003 | Bao et al. |
| 2004/0054413 A1 | 3/2004 | Higham et al. |
| 2004/0097794 A1 | 5/2004 | Bonutti |
| 2004/0097949 A1 | 5/2004 | Bonutti |
| 2004/0098016 A1 | 5/2004 | Bonutti |
| 2004/0127930 A1 | 7/2004 | Bonutti |
| 2004/0127992 A1 | 7/2004 | Serhan et al. |
| 2004/0138689 A1 | 7/2004 | Bonutti |
| 2004/0143285 A1 | 7/2004 | Bonutti |
| 2004/0225361 A1 * | 11/2004 | Glenn et al. ................ 623/17.12 |
| 2004/0249459 A1 | 12/2004 | Ferree |
| 2005/0027358 A1 * | 2/2005 | Suddaby ................ 623/17.11 |
| 2005/0043733 A1 * | 2/2005 | Eisermann et al. ............ 606/61 |
| 2005/0102030 A1 | 5/2005 | Yuksel et al. |
| 2005/0197422 A1 | 9/2005 | Mayadunne et al. |
| 2005/0209601 A1 | 9/2005 | Bowman et al. |
| 2005/0238683 A1 | 10/2005 | Adhikari et al. |
| 2005/0251259 A1 | 11/2005 | Suddaby |
| 2005/0251260 A1 | 11/2005 | Gerber et al. |
| 2005/0278023 A1 | 12/2005 | Zwirkoski |
| 2006/0051394 A1 | 3/2006 | Moore et al. |

| | | |
|---|---|---|
| 2006/0095046 A1 | 5/2006 | Trieu et al. |
| 2006/0122704 A1 | 6/2006 | Vresilovic et al. |
| 2006/0135959 A1 | 6/2006 | Yuan et al. |
| 2006/0149380 A1 | 7/2006 | Lotz et al. |
| 2006/0253198 A1 | 11/2006 | Myint et al. |
| 2006/0253199 A1 | 11/2006 | Lehuec et al. |
| 2006/0265077 A1 | 11/2006 | Zwirkoski |
| 2006/0287729 A1 | 12/2006 | Segal et al. |
| 2006/0287730 A1 | 12/2006 | Segal et al. |
| 2007/0038301 A1* | 2/2007 | Hudgins .................... 623/17.16 |
| 2007/0093903 A1 | 4/2007 | Cheng |
| 2007/0093906 A1* | 4/2007 | Hudgins et al. ............ 623/17.16 |
| 2007/0162136 A1 | 7/2007 | O'Neil et al. |
| 2007/0168041 A1 | 7/2007 | Kadiyala |
| 2007/0173943 A1 | 7/2007 | Dulak et al. |

OTHER PUBLICATIONS

Office Action (final) issued in U.S. Appl. No. 11/420,055 dated Jun. 12, 2009.

Office Action issued in U.S. Appl. No. 11/420,055 dated Sep. 4, 2009.

Office Action (final) issued in U.S. Appl. No. 11/420,055 dated Feb. 23, 2010.

German and Foley, *Minimal Access Surgical Techniques in the Management of the Painful Lumbar Motion Segment*, 30 Spine 16S, n. S52-S59 (2005).

* cited by examiner

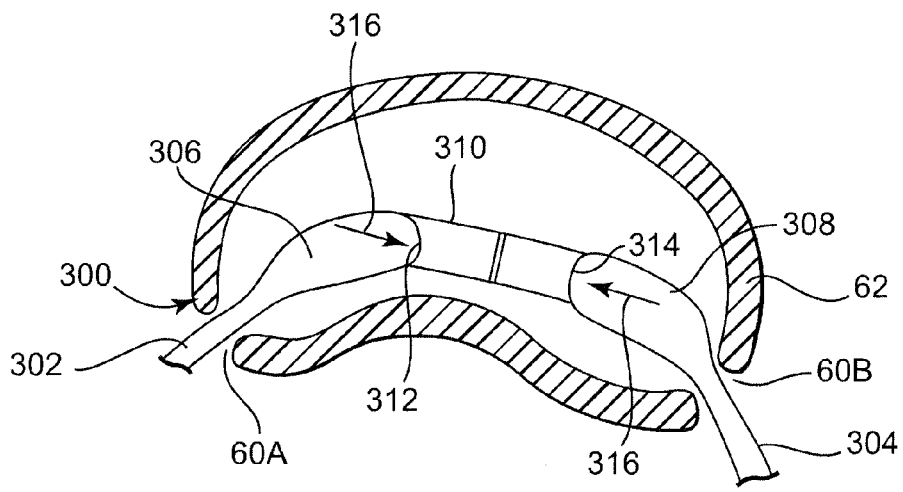
Fig. 16
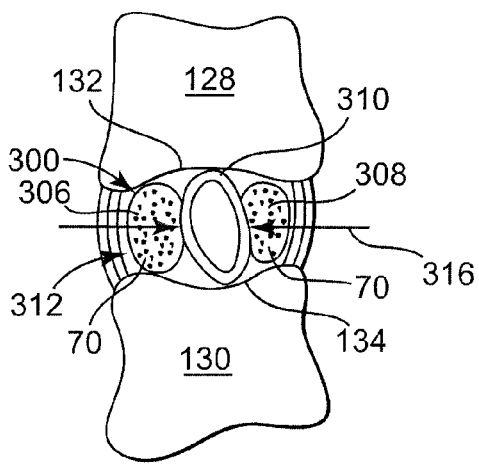 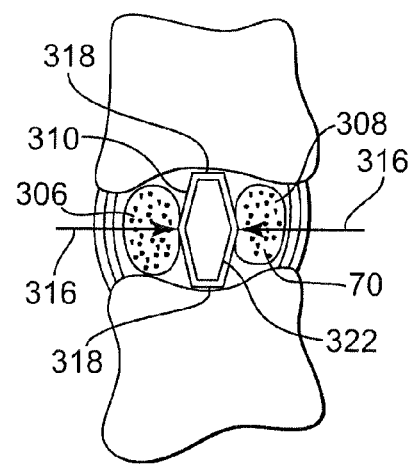
Fig. 17A    Fig. 17B

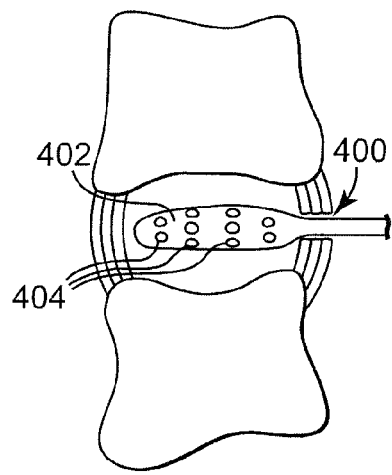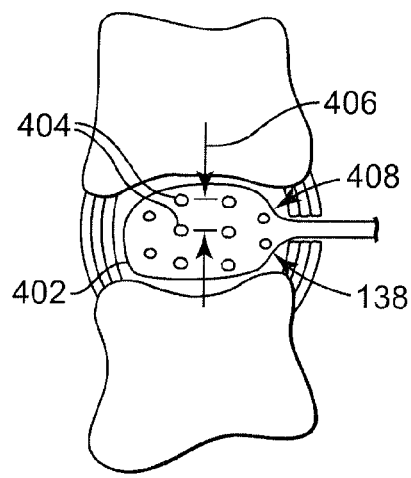
Fig. 19A  Fig. 19B
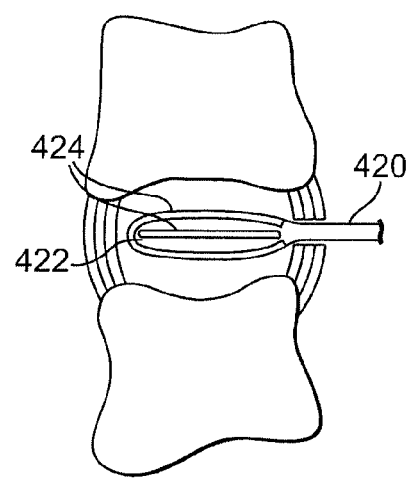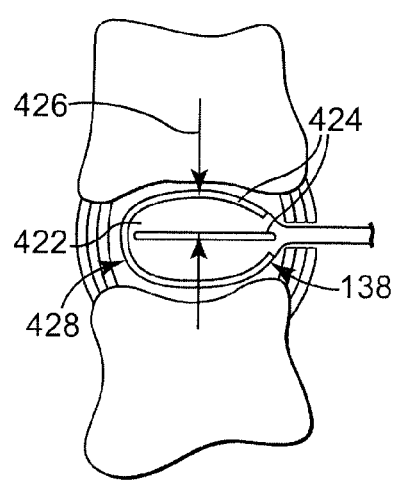
Fig. 20A  Fig. 20B

RETENTION STRUCTURE FOR IN SITU FORMATION OF AN INTERVERTEBRAL PROSTHESIS

The present application is a Continuation-In-Part of U.S. application Ser. No. 11/420,055, entitled Mold Assembly for Intervertebral Prosthesis, filed May 24, 2006, which is hereby incorporated by reference.

FIELD OF THE INVENTION

The present invention relates to various retention structures for forming an intervertebral prosthesis in situ, and in particular to a retention structure for an intervertebral disc space adapted to engage with an in situ curable biomaterial and a method of delivering the curable biomaterial.

BACKGROUND OF THE INVENTION

The intervertebral discs, which are located between adjacent vertebrae in the spine, provide structural support for the spine as well as the distribution of forces exerted on the spinal column. An intervertebral disc consists of three major components: cartilage endplates, nucleus pulposus, and annulus fibrosus.

In a healthy disc, the central portion, the nucleus pulposus or nucleus, is relatively soft and gelatinous; being composed of about 70% to about 90% water. The nucleus pulposus has high proteoglycan content and contains a significant amount of Type II collagen and chondrocytes. Surrounding the nucleus is the annulus fibrosus, which has a more rigid consistency and contains an organized fibrous network of about 40% Type I collagen, about 60% Type II collagen, and fibroblasts. The annular portion serves to provide peripheral mechanical support to the disc, afford torsional resistance, and contain the softer nucleus while resisting its hydrostatic pressure.

Intervertebral discs, however, are susceptible to disease, injury, and deterioration during the aging process. Disc herniation occurs when the nucleus begins to extrude through an opening in the annulus, often to the extent that the herniated material impinges on nerve roots in the spine or spinal cord. The posterior and posterolateral portions of the annulus are most susceptible to attenuation or herniation, and therefore, are more vulnerable to hydrostatic pressures exerted by vertical compressive forces on the intervertebral disc. Various injuries and deterioration of the intervertebral disc and annulus fibrosus are discussed by Osti et al., Annular Tears and Disc Degeneration in the Lumbar Spine, *J. Bone and Joint Surgery,* 74-B(5), (1982) pp. 678-682; Osti et al., Annulus Tears and Intervertebral Disc Degeneration, *Spine,* 15(8) (1990) pp. 762-767; Kamblin et al., Development of Degenerative Spondylosis of the Lumbar Spine after Partial Discectomy, *Spine,* 20(5) (1995) pp. 599-607.

Many treatments for intervertebral disc injury have involved the use of nuclear prostheses or disc spacers. A variety of prosthetic nuclear implants are known in the art. For example, U.S. Pat. No. 5,047,055 (Bao et al.) teaches a swellable hydrogel prosthetic nucleus. Other devices known in the art, such as intervertebral spacers, use wedges between vertebrae to reduce the pressure exerted on the disc by the spine. Intervertebral disc implants for spinal fusion are known in the art as well, such as disclosed in U.S. Pat. No. 5,425,772 (Brantigan) and U.S. Pat. No. 4,834,757 (Brantigan).

Further approaches are directed toward fusion of the adjacent vertebrate, e.g., using a cage in the manner provided by Sulzer. Sulzer's BAK® Interbody Fusion System involves the use of hollow, threaded cylinders that are implanted between two or more vertebrae. The implants are packed with bone graft to facilitate the growth of vertebral bone. Fusion is achieved when adjoining vertebrae grow together through and around the implants, resulting in stabilization.

Apparatuses and/or methods intended for use in disc repair have also been described for instance in French Patent Appl. No. FR 2 639 823 (Garcia) and U.S. Pat. No. 6,187,048 (Milner et al.). Both references differ in several significant respects from each other and from the apparatus and method described below.

Prosthetic implants formed of biomaterials that can be delivered and cured in situ, using minimally invasive techniques to form a prosthetic nucleus within an intervertebral disc have been described in U.S. Pat. No. 5,556,429 (Felt) and U.S. Pat. No. 5,888,220 (Felt et al.), and U.S. Patent Publication No. US 2003/0195628 (Felt et al.), the disclosures of which are incorporated herein by reference. The disclosed method includes, for instance, the steps of inserting a collapsed mold apparatus (which in a preferred embodiment is described as a "mold") through an opening within the annulus, and filling the mold to the point that the mold material expands with a flowable biomaterial that is adapted to cure in situ and provide a permanent disc replacement. Related methods are disclosed in U.S. Pat. No. 6,224,630 (Bao et al.), entitled "Implantable Tissue Repair Device" and U.S. Pat. No. 6,079,868 (Rydell), entitled "Static Mixer", the disclosures of which are incorporated herein by reference.

FIG. 1 illustrates an exemplary prior art catheter 11 with mold or balloon 13 located on the distal end. In the illustrated embodiment, biomaterial 23 is delivered to the mold 13 through the catheter 11. Secondary tube 11' evacuates air from the mold 13 before, during and/or after the biomaterial 23 is delivered. The secondary tube 11' can either be inside or outside the catheter 11.

BRIEF SUMMARY OF THE INVENTION

The present invention relates to an intervertebral prosthesis and method for forming an intervertebral prosthesis located in an intervertebral disc space. A retention structure and an in situ curable biomaterial combine in situ to form the intervertebral prosthesis. The present method and prosthesis can be used, for example, to implant a prosthetic disc nucleus using minimally invasive techniques that leave the surrounding disc tissue substantially intact or to implant a prosthetic total disc. The phrase intervertebral disc prosthesis is used generically to refer to both of these variations.

One embodiment is directed to an assembly for the in situ formation of a prosthesis in an intervertebral disc space between adjacent vertebrae of a patient. At least one retention structure is located in the intervertebral disc space. A distal end of at least a first lumen is located proximate the at least one retention structure. One or more in situ curable biomaterials are delivered to the intervertebral disc space through the first lumen and into engagement with the retention structure. The curable biomaterial preferably adheres to and is at least partially captured by the retention structure. Consequently, the retention structure serves to retain at least a portion of the biomaterial in the intervertebral disc space. The at least partially cured biomaterial and the at least one retention structure cooperate to comprise the prosthesis.

In one embodiment, the retention structure includes a band with openings opposite end plates of the adjacent vertebrae. The band is preferably oriented perpendicular relative to an axis of the spine to restrain the biomaterial from creating excessive pressure on the annular walls.

In another embodiment, the retention structure includes one or more collapsed retention structures adapted to expand when located in the intervertebral disc space. In another embodiment, the retention structure expands during delivery of the curable biomaterial.

The retention structure can be a discrete member or a plurality of retention structures adapted to be delivered sequentially through a lumen into the intervertebral disc space. The retention structure can be expandable and/or reorientable.

In another embodiment, the retention structure is adapted to be assembled within the intervertebral disc space. For example, the retention structure optionally includes a plurality of interlocking members that are assembled in situ. In one embodiment, the retention structure comprises a plurality of magnetic members that are assembled in situ.

The retention structure can be one or more inflatable members, woven or non-woven mesh, or coiled or kinked members. The retention structure preferably includes a plurality of tension and compression members. The retention structure may include one or more of individual strands, coils, woven or non-woven webs, open cell foams, closed cell foams, combination of open and closed cell foams, scaffolds, cotton-ball fiber matrix, or a generally honeycomb retention structure.

In another embodiment, the retention structure includes a plurality of interconnected cavities. Fluid flow devices interposed between at least some of the interconnected cavities selectively control the flow of biomaterial into at least some of the cavities. The retention structure includes a plurality of discrete cavities at least a portion of which are at least partially filled with biomaterial.

The at least partially cured biomaterial preferably substantially encapsulates the retention structure. The retention structure when in the intervertebral disc space preferably comprises at least one cross-sectional area greater than a diameter of an opening in the lumen.

The distal end of the lumen is optionally coupled to at least one retention structure. The lumen is optionally releasably attached to the retention structure. In one embodiment, at least one valve is provided to retain the biomaterial in the cavity after the lumen is removed.

One or more of the retention structure or the biomaterial optionally include a bioactive agent. In one embodiment, at least a portion of an anatomical annulus contains the retention structure and the curable biomaterial. In one embodiment, a mold optionally contains the retention structure and the curable biomaterial. The mold can be a balloon or a porous envelope.

The present invention is also directed to a method for the in situ formation of a prosthesis in an intervertebral disc space between adjacent vertebrae of a patient. The method includes locating at least one retention structure in the intervertebral disc space. A distal end of at least a first lumen is located proximate at least one retention structure. One or more flowable, curable biomaterials is delivered into the intervertebral disc space through the first lumen. The flowable biomaterial engages with the retention structure located in the intervertebral disc space so that the retention structure retains at least a portion of the biomaterial in the intervertebral disc space. The at least partially cured biomaterial and the retention structures cooperating to comprise the prosthesis.

Minimally invasive refers to a surgical mechanism, such as microsurgical, percutaneous, or endoscopic or arthroscopic surgical mechanism. In one embodiment, the entire procedure is minimally invasive, for instance, through minimal incisions in the epidermis (e.g., incisions of less than about 6 centimeters, and more preferably less than 4 centimeters, and preferably less than about 2 centimeters). In another embodiment, the procedure is minimally invasive only with respect to the annular wall and/or pertinent musculature, or bony structure. Such surgical mechanism are typically accomplished by the use of visualization such as fiber optic or microscopic visualization, and provide a post-operative recovery time that is substantially less than the recovery time that accompanies the corresponding open surgical approach. Background on minimally invasive surgery can be found in German and Foley, *Minimal Access Surgical Techniques in the Management of the Painful Lumbar Motion Segment,* 30 SPINE 16S, n. S52-S59 (2005).

Retention structure generally refers to the portion or portions of the present invention used to receive, constrain, shape and/or retain a flowable biomaterial in the intervertebral disc space during curing the biomaterial in situ. A retention structure may include or rely upon natural tissues (such as the annular shell of an intervertebral disc or the end plates of the adjacent vertebrae) for at least a portion of its conformation or function. For example, the retention structure may form a fully enclosed cavity or chamber or may rely on natural tissue for a portion thereof. The retention structure, in turn, is responsible, at least in part, for determining the position and final dimensions of the cured prosthetic implant. As such, its dimensions and other physical characteristics can be predetermined to provide an optimal combination of such properties as the ability to be delivered to a site using minimally invasive means, filled with biomaterial, control moisture contact, and optionally, then remain in place as or at the interface between cured biomaterial and natural tissue. In a particularly preferred embodiment the retention structure can itself become integral to the body of the cured biomaterial.

In some embodiments, the retention structure may be used in combination with a mold. Mold generally refers to a flexible member including at least one cavity for the receipt of biomaterial and at least one lumen to that cavity. Multiple molds, either discrete or connected, may be used in some embodiments. Some or all of the material used to form the mold will generally be retained in situ, in combination with the cured biomaterial, while some or the entire lumen will generally be removed upon completion of the procedure. The mold and/or lumens can be biodegradable or bioresorbable. Examples of biodegradable materials can be found in U.S. Publication Nos. 2005-0197422; 2005-0238683; and 2006-0051394, the disclosures of which are hereby incorporated by reference. The mold can be an impermeable, semi-permeable, or permeable membrane. In one embodiment, the mold is a highly permeable membrane, such as for example a woven or non-woven mesh or other durable, loosely woven fabrics. The mold and/or biomaterial can include or be infused with drugs, pH regulating agents, pain inhibitors, and/or growth stimulants.

Biomaterial generally refers to a material that is capable of being introduced to the site of a joint and cured to provide desired physical-chemical properties in vivo. In a preferred embodiment the term will refer to a material that is capable of being introduced to a site within the body using minimally invasive means, and cured or otherwise modified in order to cause it to be retained in a desired position and configuration. Generally such biomaterials are flowable in their uncured form, meaning they are of sufficient viscosity to allow their delivery through a lumen of on the order of about 1 mm to about 10 mm inner diameter, and preferably of about 2 mm to about 6 mm inner diameter. Such biomaterials are also curable, meaning that they can be cured or otherwise modified, in situ, at the tissue site, in order to undergo a phase or chemical change sufficient to retain a desired position and configuration.

The method and apparatus of the present invention uses one or more discrete access points or annulotomies into the intervertebral disc space, and/or through the adjacent vertebrae. The annulotomies facilitate performance of the nuclectomy, imaging or visualization of the procedure, delivery of the retention structure and biomaterial through one or more lumens, drawing a vacuum on a mold before, during and/or after delivery of the biomaterial, and securing the prosthesis in the intervertebral disc space during and after delivery of the biomaterial.

BRIEF DESCRIPTION OF THE SEVERAL VIEWS OF THE DRAWING

FIG. 16 is a cross-sectional view of an annulus containing a mold assembly with multiple molds and a pressure activated retention structure in accordance with the present invention.

FIGS. 17A and 17B are cross-sectional views of an annulus containing variations of the mold assembly of FIG. 16.

FIGS. 19A and 19B are cross-sectional views of an annulus containing a mold assembly with patterned radiopaque markers in accordance with the present invention.

FIGS. 20A and 20B are cross-sectional views of an annulus containing a mold assembly with an alternate patterned radiopaque markers in accordance with the present invention.

DETAILED DESCRIPTION OF THE INVENTION

Figure 1:
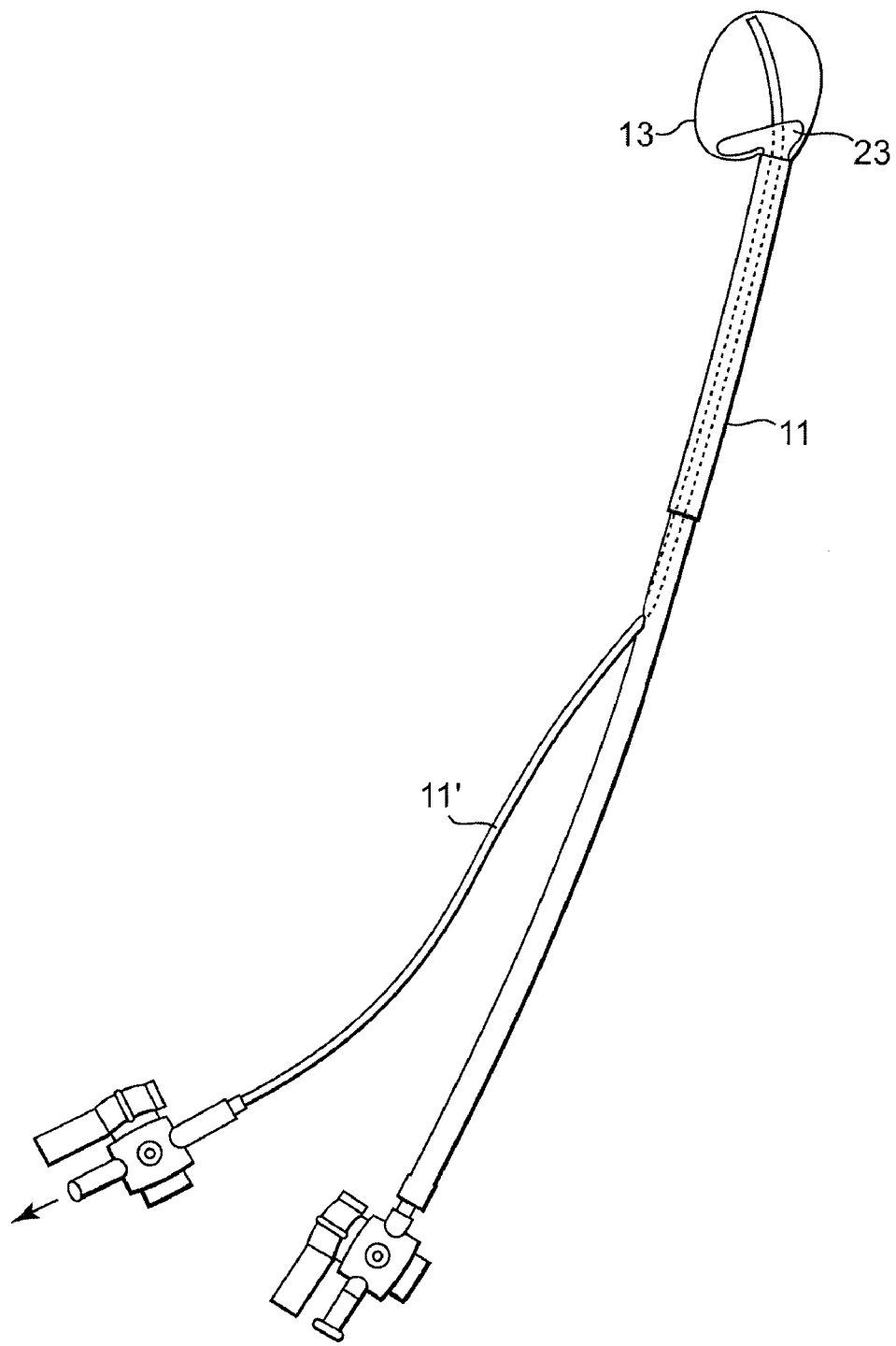
FIG. 1 is an exemplary prior art catheter and mold.
Figure 2:
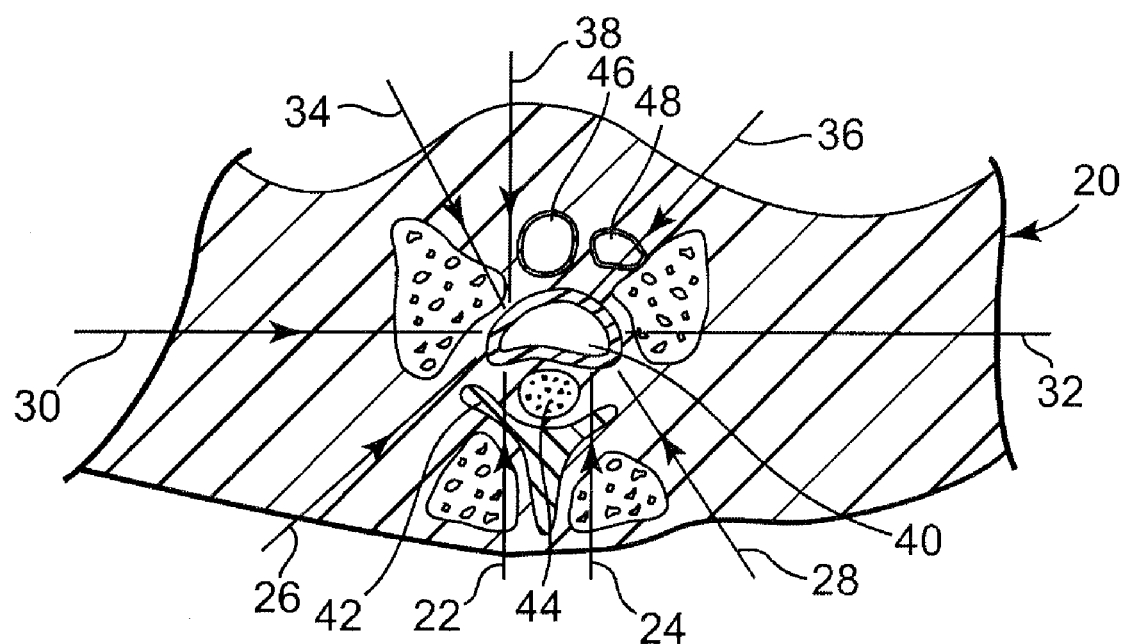
FIG. 2 is a schematic illustration of various entry paths for use in accordance with the present invention.

FIG. 2 is a cross-sectional view of a human body 20 showing various access paths 22 through 38 to the intervertebral disc 40 for performing the method of the present invention. The posterior paths 22, 24 extend either between superior and inferior transverse processes 42, or between the laminae (interlaminar path) on either side of the spinal cord 44. The posterolateral paths 26, 28 are also on opposite sides of the spinal cord 44 but at an angle of about 35-45 degrees relative to horizontal relative to the posterior paths 22, 24. The lateral paths 30, 32 extend through the side of the body. The anterior path 38 and anterolateral path 34 extend past the aorta iliac artery 46, while the anterolateral path 36 is offset from the inferior vena cava, iliac veins 48.

Depending on the disc level being operated on, and the patient anatomy. Generally, the aorta and vena cava split at the L4 vertebral body. At L5 SI the approach is typically a midline anterior approach. At L4/5 the approach may be either midline anterior or anterolateral, depending on the patient anatomy and how easy it is to retract the vessels. In some usages, the anterior approach is deemed a midline approach and the anterolateral approach is deemed an angled approach offset from the midline anterior approach.

The present method and apparatus use one or more of the access paths 22 through 38. While certain of the access paths 22 through 38 may be preferred depending on a number of factors, such as the nature of the procedure, any of the access paths can be used with the present invention.

In one embodiment, delivery catheter instruments are positioned along two or more of the access paths 22 through 38 to facilitate preparation of the intervertebral disc 40. Preparation includes, for example, formation of two or more annulotomies through the annular wall, removal of some or all of the nucleus pulposus to form a nuclear cavity, imaging of the annulus and/or the nuclear cavity, and positioning of the present multi-lumen mold in the nuclear cavity. In another embodiment, the present multi-lumen mold is positioned in the intervertebral disc 40 without use of delivery catheters.

Figure 3A:
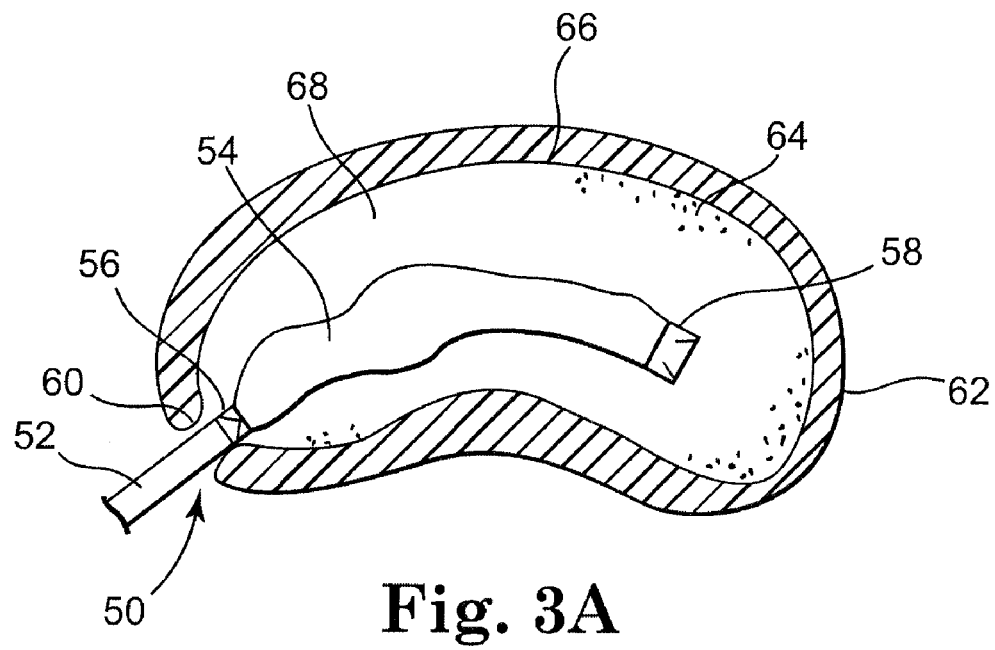
FIGS. 3A and 3B are cross-sectional views of an annulus containing a mold assembly with one or more valves in accordance with the present invention.

FIG. 3A illustrates one embodiment of a mold assembly 50 in accordance with the present invention. The mold assembly 50 includes lumen 52 fluidly coupled to mold 54. In the illustrated embodiment, valve 56 is provided at the interface between the lumen 52 and the mold 54. In one embodiment, valve 58 is optionally located at a separate location on the mold 54.

The method of using the present mold assembly 50 involves forming an annulotomy 60 at a location in the annulus 62. The nucleus pulposus 64 located in the disc space 66 is preferably substantially removed to create a nuclear cavity 68. As illustrated in FIG. 3A, some portion of the nucleus pulposus 64 may remain in the nuclear cavity 68 after the nuclectomy. The mold assembly 50 is then inserted through the annulotomy 60 so that the mold 54 is positioned in the nuclear cavity 68.

Figure 3B:
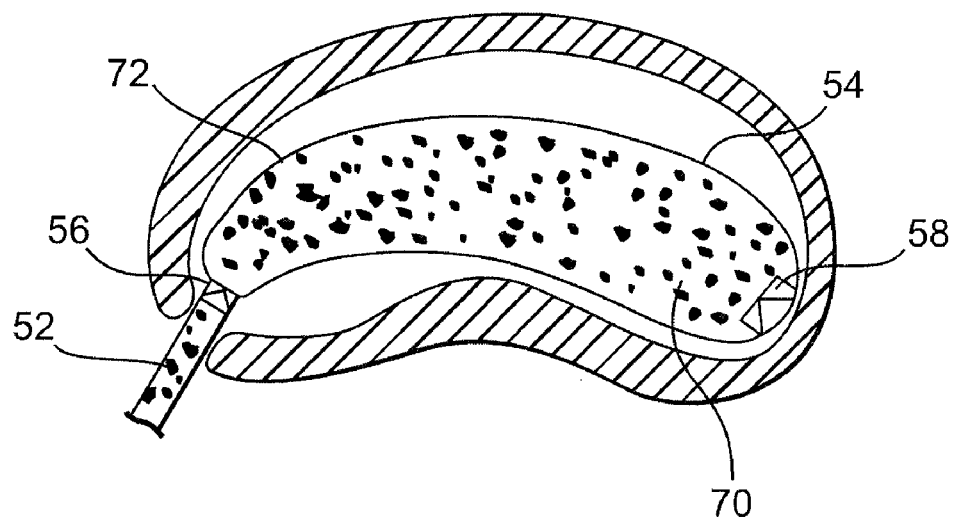

As illustrated in FIG. 3B, biomaterial 70 is delivered through the lumen 52 into the mold 54. As the biomaterial 70 progresses through the mold 54, at least a portion of the air located in the mold 54 is preferably pushed out through the valve 58. In the illustrated embodiment, the valves 56 and 58 are preferably check valves that are forced into the closed position by the pressure of the biomaterial 70. Once delivery of the biomaterial 70 is substantially completed, the lumen 52 is detached from the mold 54 removed from the annulotomy 60. In the illustrated embodiment, the valve 56 permits the lumen 52 to be separated and removed before the biomaterial 70 has cured.

In one embodiment, one or more of the mold 54, the valves 56, 58, and/or the lumens 52 have radiopaque properties that facilitate imaging of the prosthesis 72 being formed. In another embodiment, the lumen 52 is releasably attached to the valve 56 to facilitate removal.

In one embodiment, the lumen 52 is threaded to the valve 56. In another embodiment, a quick release interface is used to attach the lumen 52 to the valve 56.

Figure 3C:
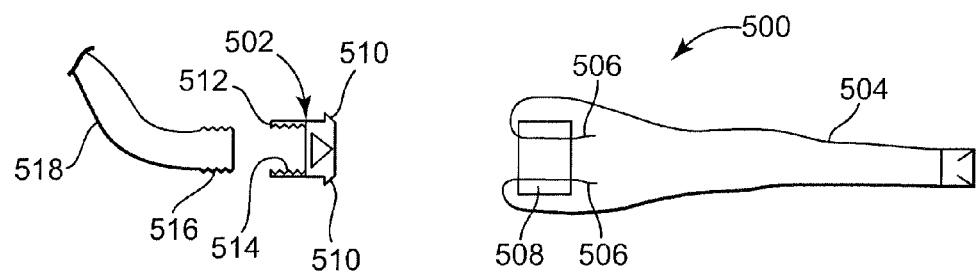
FIGS. 3C and 3D are side sectional views of a mold assembly including a connector assembly in accordance with the present invention.
Figure 3D:
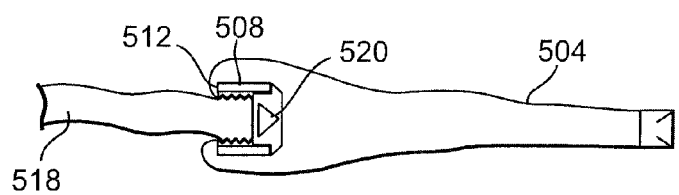

FIGS. 3C and 3D are assembly views of a mold assembly 500 with a connection assembly 502 recessed in the mold 504 in accordance with the present invention. Open end 506 of the mold 504 is inserted into sleeve 508. The connector assembly 502 is then coupled to the sleeve 508. The open end 506 is secured between the sleeve 508 and connector assembly 502. In the illustrated embodiment, distal end of the connector assembly 502 includes a mechanical interface 510 that mechanically couples with the sleeve 508. The connector assembly 502 can be coupled to the open end 506 of the mold 504 and the sleeve 508 using a variety of techniques, such as adhesives, mechanical interlocks, fasteners, and the like.

Figure 3E:
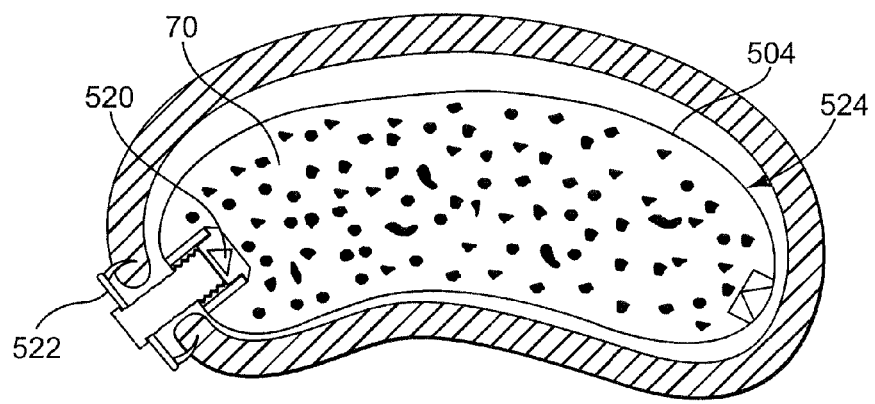
FIG. 3E is a cross-sectional view of the mold assembly of FIGS. 3C and 3D implanted in a patient.

The exposed end 512 of the connector assembly 502 preferably includes a mechanical interlock 514, such as for example internal threads, that couple with a corresponding interlock 516, such as external threads, on the lumen 518. As best illustrated in FIG. 3E, the biomaterial 70 is retained in the mold by valve 520 preferably located in the connector assembly 502. In the illustrated embodiment, the connector assembly 502 and/or the valve 520 are substantially flush with the outer surface of the mold 504. In another embodiment, the connector assembly 502 may protrude above the outer surface of the mold 504. The lumen 518 is preferably removed from the mold assembly 500 before the biomaterial 70 is cured. The exposed mechanical interlock 514 on the connector assembly 502 can optionally be used to attach a securing device 522 to the prosthesis 524.

Figure 4A:
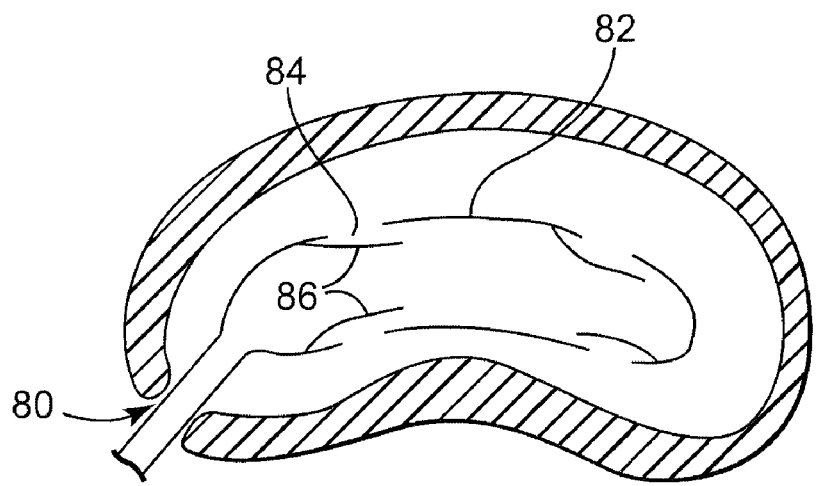
FIGS. 4A and 4B are cross-sectional views of an annulus containing a mold assembly with an alternate valves in accordance with the present invention.
Figure 4B:
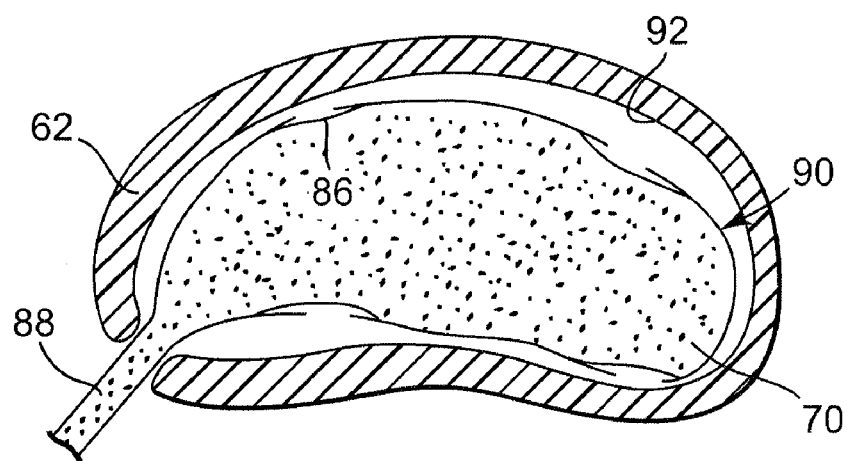

FIG. 4A illustrates an alternate mold assembly 80 in accordance with the present invention. Mold 82 includes a plurality of openings 84. The openings 84 can be any shape and a variety of sizes. Internal flaps 86 are located over the openings 84. As best illustrated in FIG. 4B, biomaterial 70 is delivered through lumen 88 to the mold 82. Pressure from the biomaterial 70 presses the flaps 86 against the openings 84, substantially sealing the biomaterial 70 within the mold 82.

In one embodiment, the flaps 86 permit any air or biomaterial in the mold 82 to be pushed out through the openings 84 during delivery of the biomaterial 70. In another embodiment, the flaps 86 to not completely seal the openings 84 until the mold 82 is substantially inflated and pressing against inner surface 92 of the annulus 62.

The flaps 86 can be constructed from the same or different material than the mold 82. In one embodiment, the flaps 86 are constructed from a radiopaque material that is easily visible using various imaging technologies. Prior to the delivery of the biomaterial 70, such as illustrated in FIG. 4A, the spacing between the flaps 86 indicates that the mold 82 is not inflated. After delivery of the biomaterial 70, such as illustrated in FIG. 4B, the spacing between the flaps 86 provides an indication of the shape and position of the intervertebral prosthesis 90 relative to the annulus 62. By strategically locating the openings 84 and flaps 86 around the outer surface of the mold 82, a series of images can be taken during delivery of the biomaterial 70 which will illustrate the prosthesis 90 during formation and provide reference points for evaluating whether the prosthesis 90 is properly positioned and fully inflated within the annulus 62.

Figure 5A:
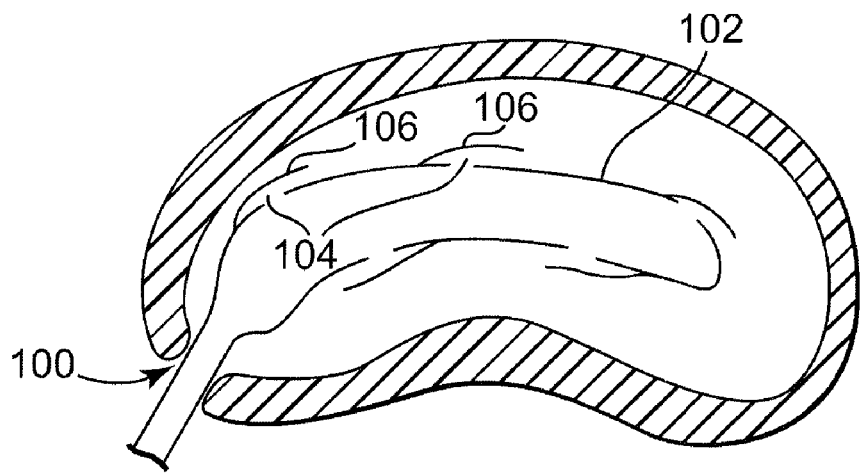
FIGS. 5A and 5B are cross-sectional views of an annulus containing a mold assembly with alternate valves in accordance with the present invention.
Figure 5B:
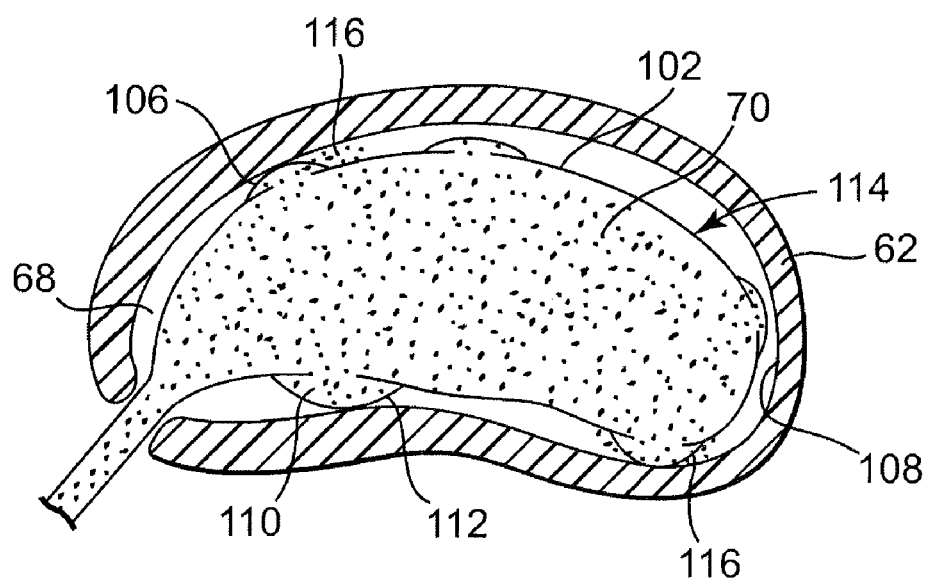

FIG. 5A illustrates an alternate mold assembly 100 in accordance with the present invention. Mold 102 includes a plurality of openings 104 with corresponding external flaps or valves 106. As best illustrated in FIG. 5B, delivery of the biomaterial 70 causes the mold 102 to inflate. When the mold 102 is substantially inflated, the flaps 106 are pressed against the openings 104 by interior surface 108 of the nuclear cavity 68.

In the illustrated embodiment, portion 110 of the biomaterial 70 forms a raised structure 112 over some or all of the openings 104. These raised structures serve to anchor the resulting prosthesis 114 in the nuclear cavity 68. Other examples of raised structures include barbs, spikes, hooks, and/or a high friction surface that can facilitate attachment to soft tissue and/or bone. Also illustrated in FIG. 5B, portion 116 of the biomaterial 70 optionally escapes from the mold 102 prior to the flaps 106 being pressed against the openings 104. The portion 116 of the biomaterial 70 serves to adhere the prosthesis 114 to the inner surface 108 of the annulus 62. Again, one or more of the mold 102, the flaps 106 may include radiopaque properties.

Figure 6A:
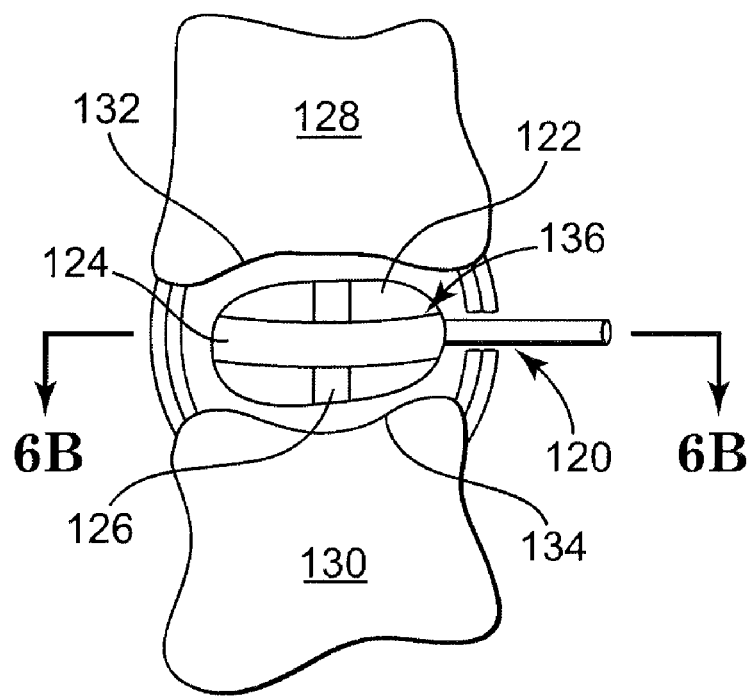
FIGS. 6A and 6B are cross-sectional views of an annulus containing a retention structure in the form of bands in accordance with the present invention.
Figure 6B:
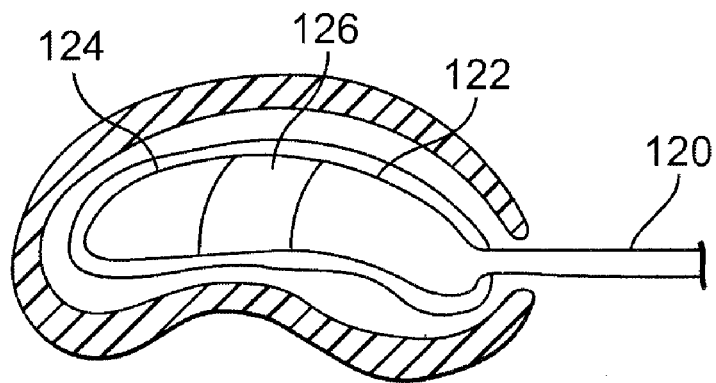

FIGS. 6A and 6B illustrate a prosthesis 136 including one or more retention structures 124, 126. In the illustrated embodiment, retention structure 124 is positioned horizontally between adjacent vertebrae 128, 130. Retention structure 126 is oriented perpendicular to the retention structure. Lumen 120 is preferably engaged with one or both of the retention structures 124, 126.

The retention structure preferably limits the amount of pressure the resulting prosthesis 136 places on the annular walls 62. A compressive force placed on the prosthesis 136 by the end plates 132, 134 is directed back towards the end plates, rather than horizontally into the annular wall 62. The retention structure preferably limits inflation of the mold 122 in the vertical direction. The retention structure can optionally be used to set a maximum disc height or separation between the adjacent vertebrae 128, 130 when the mold 122 is fully inflated.

In the illustrated embodiment, the retention structure 124, 126 are preferably radiopaque. As with the flaps 86, 106 of FIGS. 4 and 5, the retention structure 124, 126 provide an indication of the shape and position of the prosthesis 136 in the intervertebral disc space 138. As the biomaterial is delivered, the retention structures 124, 126 are deployed and positioned in accordance with the requirements of the prosthesis 136. A series of images can be taken of the intervertebral disc space 138 to map the progress of the prosthesis formation. Because the size and width of the retention structure 124, 126 are known prior to the procedure, the resulting images provide an accurate picture of the position of the prosthesis 136 relative to the vertebrae 128, 130.

In one embodiment, the retention structures 124, 126 are used in combination with mold 122. In an alternate embodiment, one or both of the retention structures 124, 126 can be located at the interior of the mold 122. The retention structures 124, 126 can optionally be attached to the mold 122.

Figure 6C:
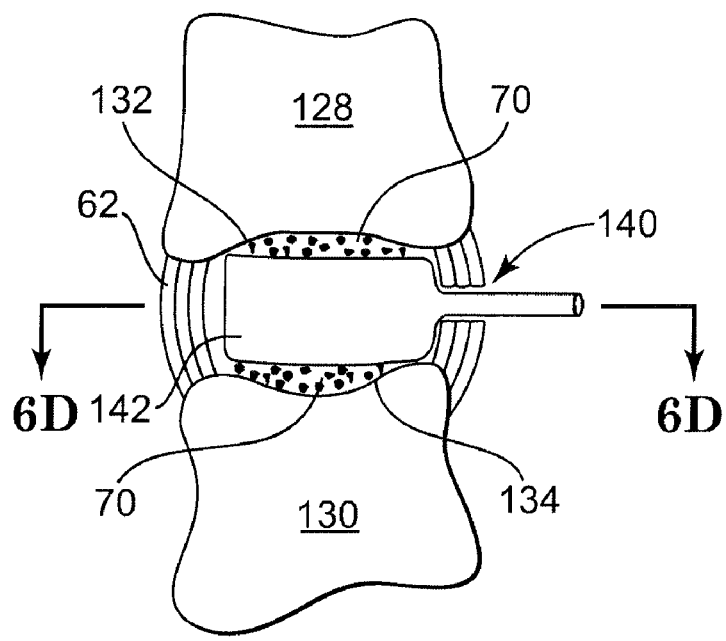
FIGS. 6C and 6D are cross-sectional views of an annulus containing a mold assembly comprising a retention structure in accordance with the present invention.
Figure 6D:
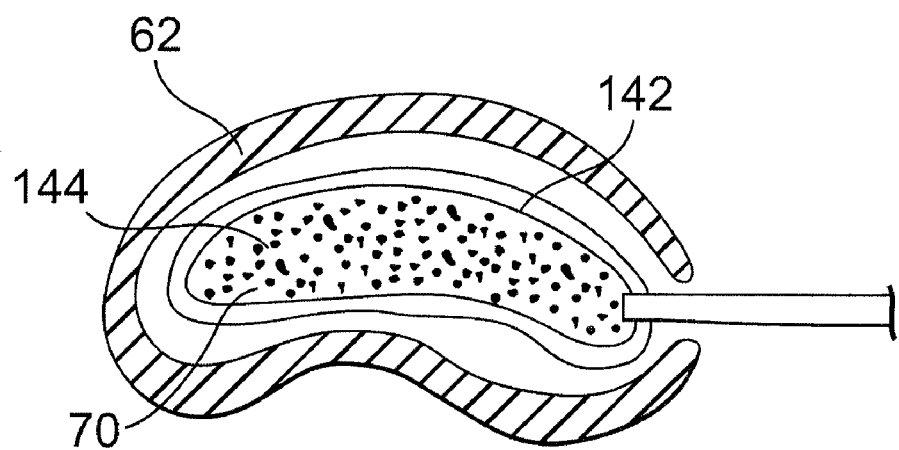

FIGS. 6C and 6D illustrate a retention structure 142 in accordance with the present invention. The retention structure 142 is preferably positioned horizontally between adjacent vertebrae 128, 130. In the illustrated embodiment, the retention structure 142 also serves as a mold for retaining at least a portion of the biomaterial 70. The annulus wall 62 may also act to retain the biomaterial 70 in the intervertebral disc space.

In one embodiment, the retention structure 142 preferably extends to the endplates 132, 134 so that the biomaterial 70 is substantially retained in center region 144 formed by the retention structure 142. In the embodiment of FIG. 6C, the biomaterial 70 extends above and below the retention structure 142 to engage with the endplates 132, 134. As best illustrated in FIG. 6D, the retention structure 142 is open at the top and bottom. In some embodiments, the biomaterial 70 may flow around the outside perimeter of the retention structure 142.

Figure 7A:
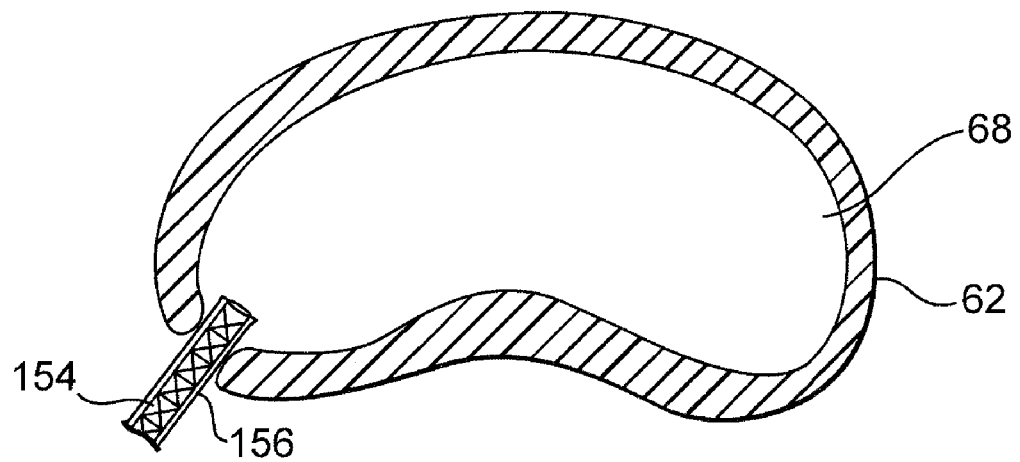
FIGS. 7A and 7B are cross-sectional views of an annulus containing a prosthesis with an expandable retention structure in accordance with the present invention.
Figure 7B:
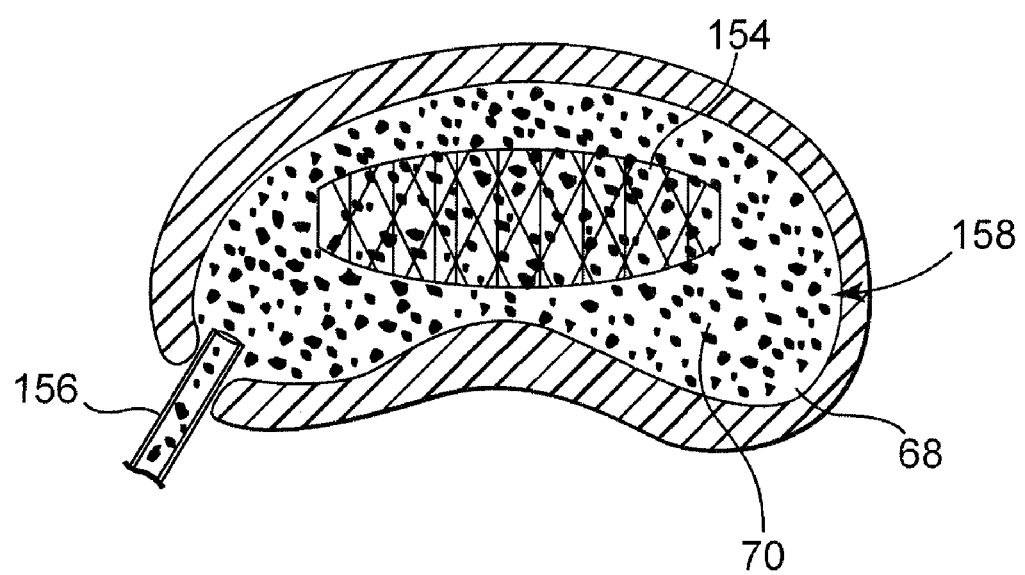

FIGS. 7A and 7B illustrate an alternate prosthesis 158 in accordance with the present invention. Retention structure 154 configured in a compressed state is delivered into the nuclear cavity 68 of the annulus 62 through delivery lumen 156.

As best illustrated in FIG. 7B, once the retention structure 154 is released from the delivery lumen 156, it assumes its original expanded shape within the nuclear cavity 68. The biomaterial 70 is delivered to the nuclear cavity 68, where it flows into and around the retention structure 154. The retention structure 154 serves to retain at least a portion of the biomaterial in the nuclear cavity 68 by surface tension, adhesion, mechanical capture, friction, viscosity, and a variety of other mechanisms. In an alternate embodiment, the retention structure 154 is deployed by the pressure of the biomaterial 70 being delivered into the nuclear cavity 68.

In the illustrated embodiment, the retention structure 154 is a mesh woven to form a generally tubular structure. The mesh 154 can be constructed from a variety of metal, polymeric, biologic, and composite materials suitable for implantation in the human body. In one embodiment, the mesh operates primarily as a tension member within the prosthesis 158. Alternatively, the retention structure 154 is configured to act as both a tension and compression member within the prosthesis 158.

In another embodiment, the retention structure 154, or portions thereof, are constructed from a radiopaque material. In the expanded configuration illustrated in FIG. 7B, the radiopaque elements of the retention structure 154 provide a grid or measuring device that is readily visible using conventional imaging techniques. The retention structure 154 thus provides a way to determine the shape, volume, dimensions, and position of the prosthesis 158 in the annular cavity 68.

Figure 8:
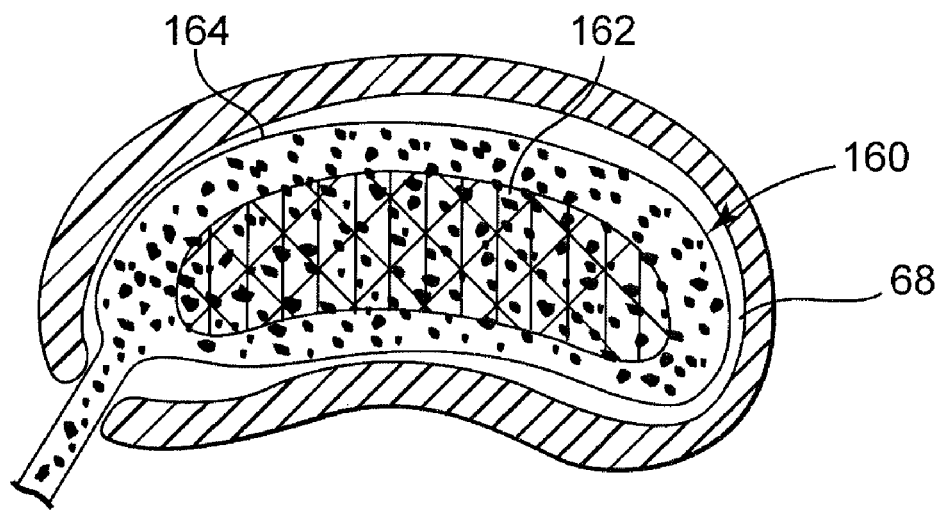
FIG. 8 is a cross-sectional view of an annulus containing a prosthesis with an expandable retention structure in a mold in accordance with the present invention.

FIG. 8 illustrates an alternate prosthesis 160 with an internal retention structure 162 having a shape generally corresponding to the nuclear cavity 68. As illustrated in FIG. 7, the retention structure 162 is compressed within the delivery lumen 156 (see FIG. 7A) and delivered into mold 164 located in the nuclear cavity 68. Once in the expanded configuration illustrated in FIG. 8, the retention structure 162 can operate as a tension and/or compression member within the prosthesis 160.

Figure 9:
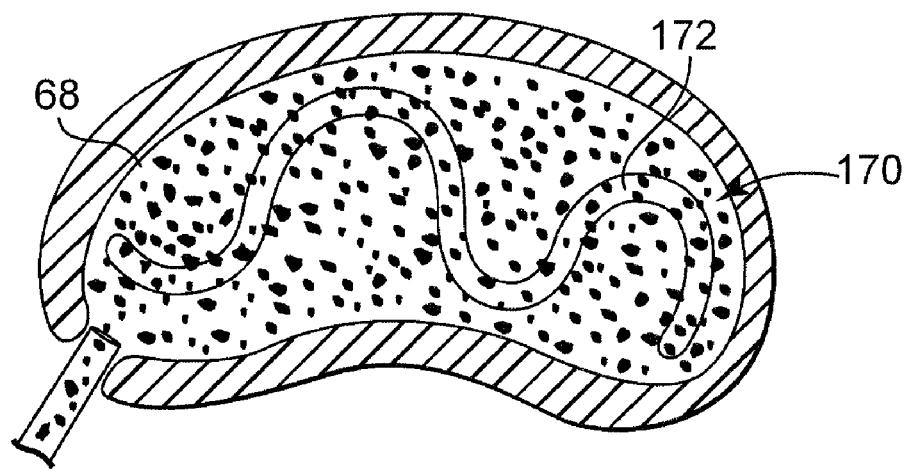
FIG. 9 is a cross-sectional view of an annulus containing a prosthesis with an alternate expandable retention structure in accordance with the present invention.

FIG. 9 illustrates an alternate prosthesis 170 in accordance with the present invention. Retention structure 172 is again positioned in the nuclear cavity 68 in a compressed configuration through a delivery lumen 156 (see FIG. 7A). The retention structure 172 is preferably constructed of a shape memory alloy (SMA), such as the nickel-titanium alloy Nitinol or of an elastic memory polymer that assumes a predetermined shape once released from the delivery lumen 156 or once a certain temperature is reached, such as for example the heat of the body. In the preferred embodiment, the retention structure 172 has radiopaque properties which can be used to facilitate imaging of the prosthesis 170.

In another embodiment, the retention structure 172 is a mold configured with a coil shape. When inflated with biomaterial 70, the mold forms a coil-shaped retention structure. Additional biomaterial 70 is preferably delivered around the coil structure 172.

Figure 10A:
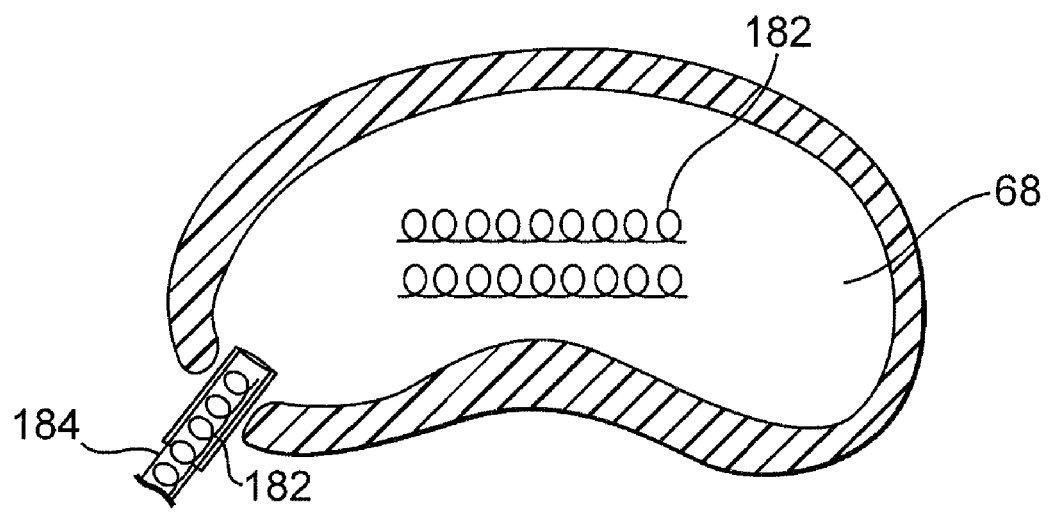
FIGS. 10A and 10B are cross-sectional views of an annulus containing a prosthesis with a plurality of helical coils assembled into a retention structure in accordance with the present invention.
Figure 10B:
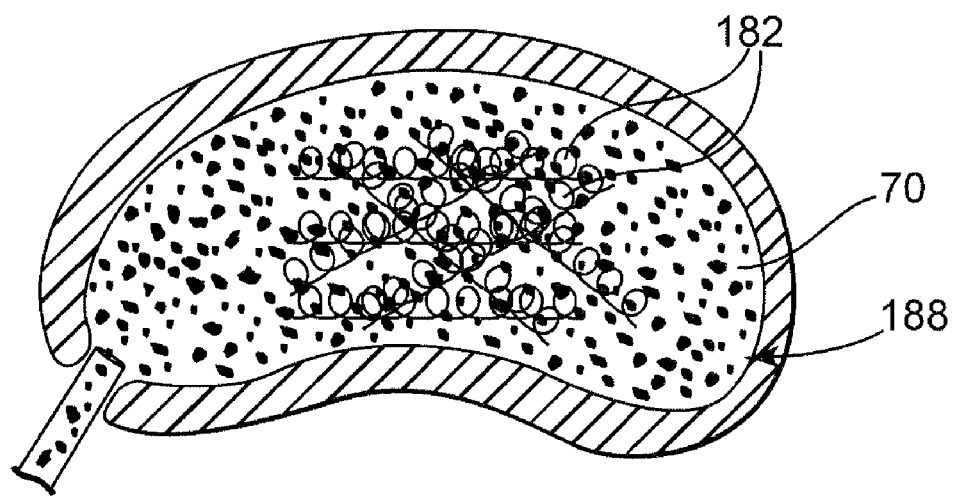

FIGS. 10A and 10B illustrate an alternate prosthesis 188 in accordance with the present invention. A plurality of discrete helical retaining structures 182 are delivered through a delivery lumen 184 into the annular cavity 68. As best illustrated in FIG. 10B, the helical retaining structures 182 intertwine and become entangled within the annular cavity 68. In one embodiment, the helical retaining structures 182 are rotated during insertion to facilitate engagement with the retaining structures 182 already in the annular cavity 68.

Alternatively, these retaining structures 182 can be kinked strands, which when compressed have a generally longitudinal orientation to provide easy delivery through the lumen 184. Once inside the annular cavity 68, the retaining structures 182 are permitted to expand or reorient. The cross-sectional area of the retaining structures 182 in the expanded or reoriented state is preferably greater than the diameter of the lumen 184, so as to prevent ejection during delivery of the biomaterial 70.

The plurality of retaining structures 182 are preferably discrete structures that act randomly and can be positioned independently. The discrete retaining structures 182 of the present invention can be delivered sequentially and interlocked or interengaged in situ. Alternatively, groups of the retaining structures 182 can be delivered together.

Once the biomaterial 70 is delivered and at least partially cured, the relative position of the retaining structures 182 is set. The retaining structures 182 can act as spring members to provide additional resistance to compression and as tension members within the prosthesis 188. Some or all of the helical retaining structures 182 preferably have radiopaque properties to facilitate imaging of the prosthesis 188.

Figure 11A:
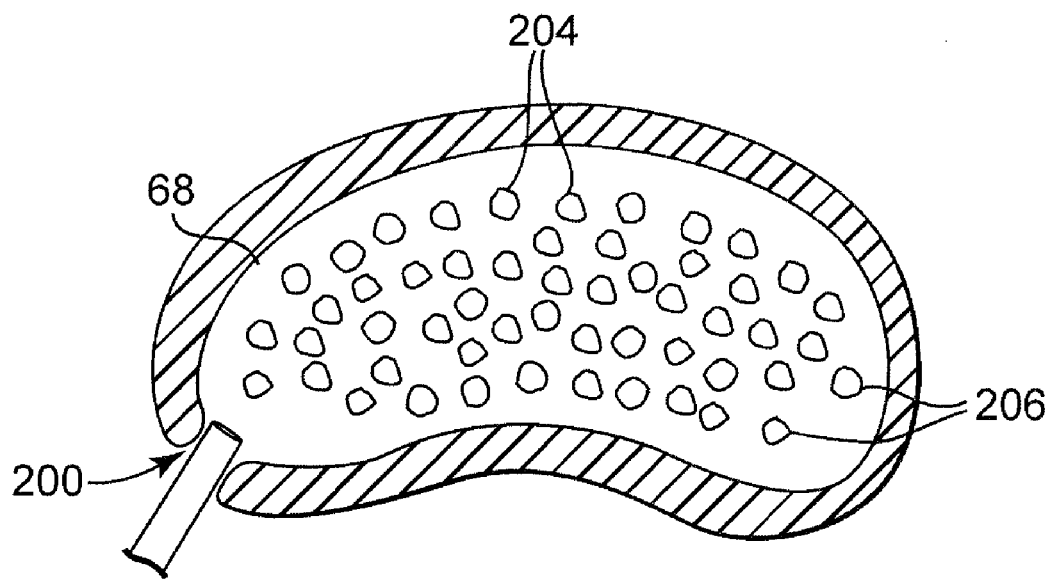
FIGS. 11A and 11B are cross-sectional views of an annulus containing a prosthesis with a plurality of spherical retention structures in accordance with the present invention.
Figure 11B:
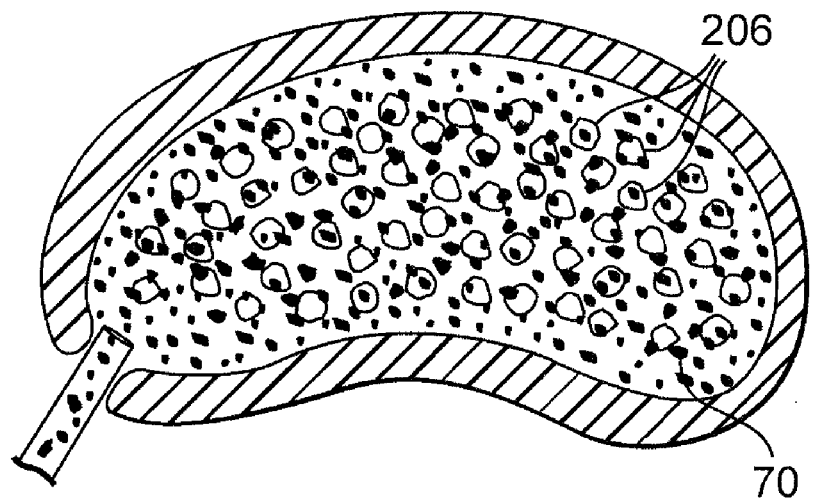

FIGS. 11A and 11B illustrate an alternate prosthesis 200 in accordance with the present invention. A plurality of retaining structures 204 are delivered into the nuclear cavity 68. Biomaterial 70 is then delivered to the nuclear cavity 68. The retention structures 204 assist in holding the biomaterial 70 in place. The retention structures 204 typically arrange themselves randomly within the intervertebral disc space 202.

In the illustrated embodiment, the retention structures 204 are a plurality of spherical members 206. The spherical members 206 flow and shift relative to each other within the intervertebral disc space 202. In one embodiment, the spherical members 206 are constructed from metal, ceramic, and/or polymeric materials. The spherical members 206 can also be a multi-layered structure, such as for example, a metal core with a polymeric outer layer.

In another embodiment, the spherical members 206 are hollow shells with openings into which the biomaterial 70 can flow. In this embodiment, the biomaterial 70 fills the hollow interior of the spherical members 206 and bonds adjacent spherical members 206 to each other.

In one embodiment, the spherical members 206 have magnetic properties so they clump together within the intervertebral disc space 202 before the biomaterial 70 is delivered. Some or all of the spherical members 206 optionally have radiopaque properties.

Figure 12:
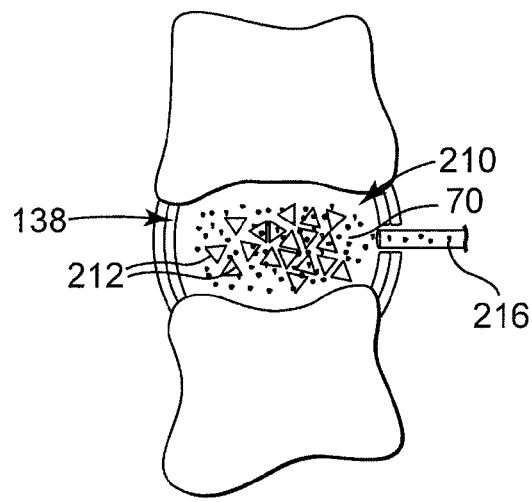
FIG. 12 is a cross-sectional view of an annulus containing a prosthesis with an assembled retention structure in accordance with the present invention.

FIG. 12 is a side sectional view of an intervertebral disc space 138 containing prosthesis 210 in accordance with the present invention. A plurality of polyhedron retention structures 212 are delivered into the intervertebral disc space 138 through lumen 216. For example, the retention structure can be pyramidal, tetrahedrons, and the like. In one embodiment, the pyramidal retention structures 212 have magnetic properties causing them to bind to each other within the intervertebral disc space 138. In another embodiment, the pyramidal retention structures 212 include a plurality of holes or cavities into which the biomaterial 70 flows, securing the retention structures 212 relative to each other and relative to the prosthesis 210.

Figure 13:
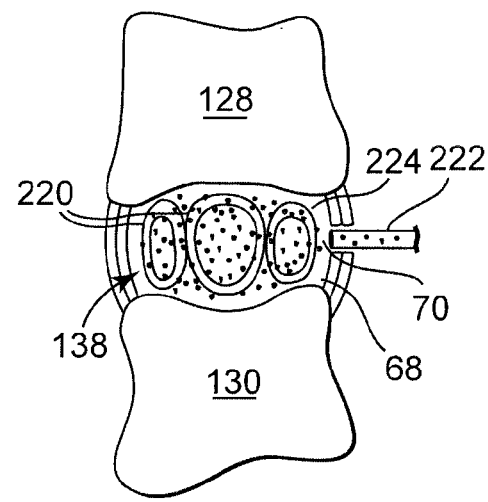
FIG. 13 is a cross-sectional view of an annulus containing a prosthesis with an alternate assembled retention structure in accordance with the present invention.

FIG. 13 is a side sectional view of an intervertebral disc space 138 with prosthesis 224 having coiled or loop shaped retention structures 220 in accordance with the present invention. The retention structures 220 can be compressed for delivery through the lumen 222, and allowed to expand once inside the nuclear cavity 68. Biomaterial 70 is then injected to secure the relative position of the retention structures 220 within the prosthesis 224.

The retention structures 220 are preferably constructed from a spring metal that helps maintain the separation between the adjacent vertebrae 128, 130. In one embodiment, the retention structures 220 are resilient and flex when loaded. In an alternate embodiment, the retention structures 220 are substantially rigid in at least one direction, while being compliant in another direction to permit insertion through the lumen 222. The retention structures 220 optionally define a minimum separation between the adjacent vertebrae 128, 130. The retention structures 220 can operate as tension and/or compression members.

Figure 14:
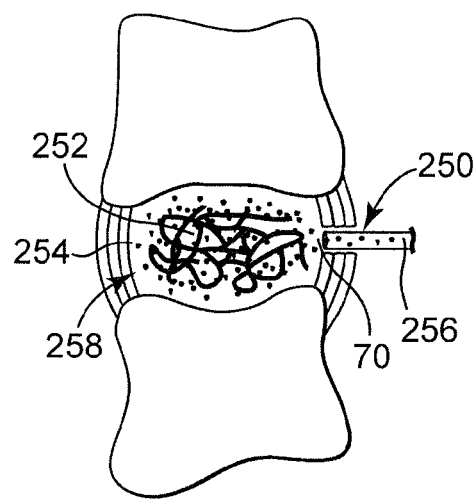
FIG. 14 is a cross-sectional view of an annulus containing a prosthesis with a fibrous retention structure in accordance with the present invention.

FIG. 14 is a side sectional view of an alternate prosthesis 258 in accordance with the present invention. A plurality of reinforcing fibers 252 are delivered into the intervertebral disc space 254 through lumen 256. The biomaterial 70 is then delivered and secures the relative position of the reinforcing fibers 252 within the intervertebral disc space 138. The reinforcing fibers 252 can be in the form of individual strands, coils, woven or non-woven webs, open cell foams, closed cell foams, combination of open and closed cell foams, scaffolds, cotton-ball fiber matrix, or a variety of other structures. The reinforcing fibers 252 can be constructed from metal, ceramic, polymeric materials, or composites thereof. The reinforcing fibers 252 can operate as tension and/or compression members within prosthesis 258.

Figure 15A:
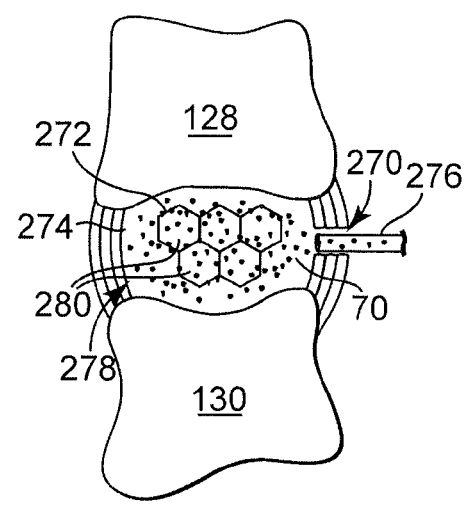
FIG. 15A is a cross-sectional view of an annulus containing a prosthesis with an expandable honeycomb retention structure in accordance with the present invention.

FIG. 15A is a side sectional view of an alternate prosthesis 278 in accordance with the present invention. A three-dimensional honeycomb structure 272 is compressed and delivered into the intervertebral disc space 274 through the lumen 276. Once in the expanded configuration, illustrated in FIG. 15A, the biomaterial 70 is delivered, fixing the honeycomb structure 272 in the illustrated configuration. In another embodiment, the delivery of the biomaterial expands or inflates the honeycomb structure 272.

The biomaterial 70 flows around and into the honeycomb structure 272 providing a highly resilient prosthesis 278. In one embodiment, the honeycomb structure 272 still retains its capacity to flex along with the biomaterial 70 when compressed by the adjacent vertebrae 128, 130. The honeycomb structure 272 can be constructed from a plurality of interconnected tension and/or compression members. In yet another embodiment, the honeycomb structure is an open cell foam.

In one embodiment, the honeycomb structure 272 has fluid flow devices, such as for example pores, holes of varying diameter or valves, interposed between at least some of the interconnected cavities 280. The fluid flow devices selectively controlling the flow of biomaterial 70 into at least some of the cavities 280 or filling the cavities 280 differentially, thus combining the different mechanical properties of the honeycomb structure 272 with the biomaterial 70 in an adaptable manner. The generally honeycomb structure 272 can optionally be combined with open or closed cell foam.

Figure 15B:
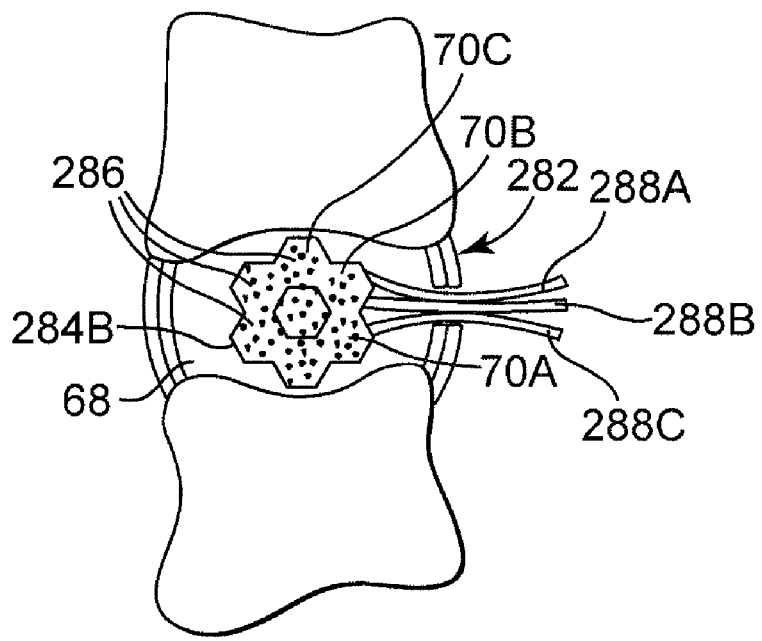
FIGS. 15B and 15C are side and top sectional views of an annulus containing a prosthesis with an alternate expandable honeycomb structure in accordance with the present invention.
Figure 15C:
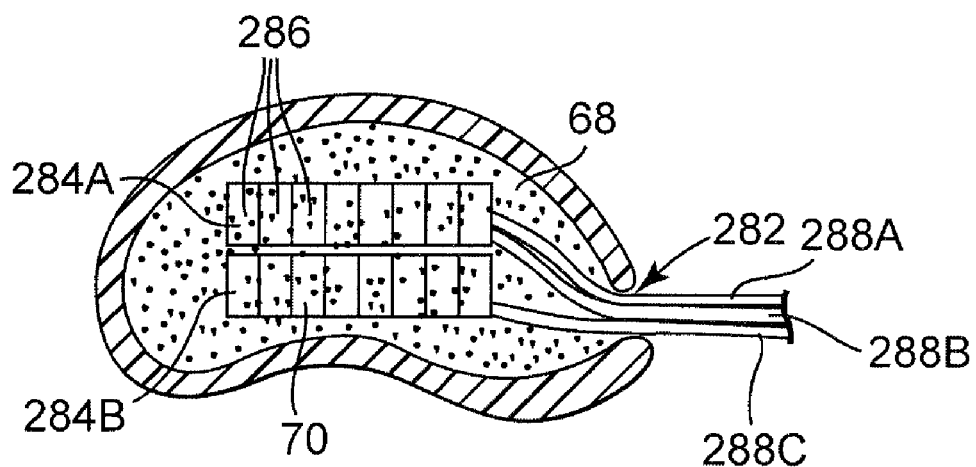

FIGS. 15B and 15C are side and top sectional views of a prosthesis 282 with a plurality of three-dimensional honeycomb structures 284A, 284B (referred to collectively as "284") in accordance with the present invention. The honeycomb structures 284 are constructed so that the inflow of biomaterial 70 can be selectively directed to certain cavities 286. In alternate embodiments, more than two honeycomb structures 284A, 284B can optionally be used.

In one embodiment, holes interconnecting adjacent cavities 286 can be selectively opened or closed before the honeycomb structures 284 are inserted into the patient. In another embodiment, a plurality of lumens 288A, 288B, 288C, . . . (referred to collectively as "288") are provided that are each connected to a different cavity 286. One or more of the lumens 288 can also be used to evacuate the annular cavity 68.

Selective delivery of the biomaterial 70 into the honeycomb structures 284 can be used to create a variety of predetermined internal shapes. Using a plurality of lumens 288 permits different biomaterials 70A, 70B, 70C, . . . to be delivered to different cavities 286 within the honeycomb structure 284. The biomaterials 70A, 70B, 70C, . . . can be selected based on a variety of properties, such as mechanical or biological properties, biodegradability, bioabsorbability, ability to delivery bioactive agents. As used herein, "bioactive agent" refers to cytokines and preparations with cytokines, microorganisms, plasmids, cultures of microorganisms, DNA-sequences, clone vectors, monoclonal and polyclonal antibodies, drugs, pH regulators, cells, enzymes, purified recombinant and natural proteins, growth factors, and the like.

FIG. 16 illustrates an alternate mold assembly 300 in accordance with the present invention. In the illustrated embodiment, two annulotomies 60A, 60B are formed in the annulus 62. The mold assembly 300 is threaded through one of the annulotomies so that the lumens 302, 304 each protrude from annulotomies 60A, 60B, respectively. Lumen 302 is fluidly coupled to mold 306 while lumen 304 is fluidly coupled with mold 308. Retention structure 310 is attached to molds 306, 308 at the locations 312, 314, respectively.

FIG. 17A is a side sectional view of the mold assembly 300 of FIG. 16 implanted between adjacent vertebrae 128, 130. Biomaterial 70 is delivered to the molds 306, 308, which applies opposing compressive forces 316 on the retention structure 310. In the illustrated embodiment, the retention structure 310 is a coil, loop, or bend (arc) of resilient material, such as a memory metal, spring metal, and the like. The resulting prosthesis 312 includes a pair of molds 306, 308 containing a cured biomaterial 70 holding the retention structure 310 against adjacent end plates 132, 136 of the vertebrae 128, 130 respectively. The retention structure can serve to resist compression of the prosthesis 312 or to establish a minimum separation between the adjacent end plates 132, 134.

FIG. 17B is an alternate embodiment of the mold assembly 300 of FIG. 16. In the illustrated embodiment, retention structure 310 includes a series of fold lines or hinges 318. Expansion of the molds 306, 308 with biomaterial 70 generates forces 316 that converts the generally flat retention structure 310 (see FIG. 16) into the shaped retention structure 322 illustrated in FIG. 17B. Alternatively, the hinge 318 could be facing the molds 306, 308 rather than the endplates. In the embodiments of FIGS. 17A and 17B, delivery of the biomaterial 70 deploys the retention structure 310 to an expanded configuration.

Figure 18A:
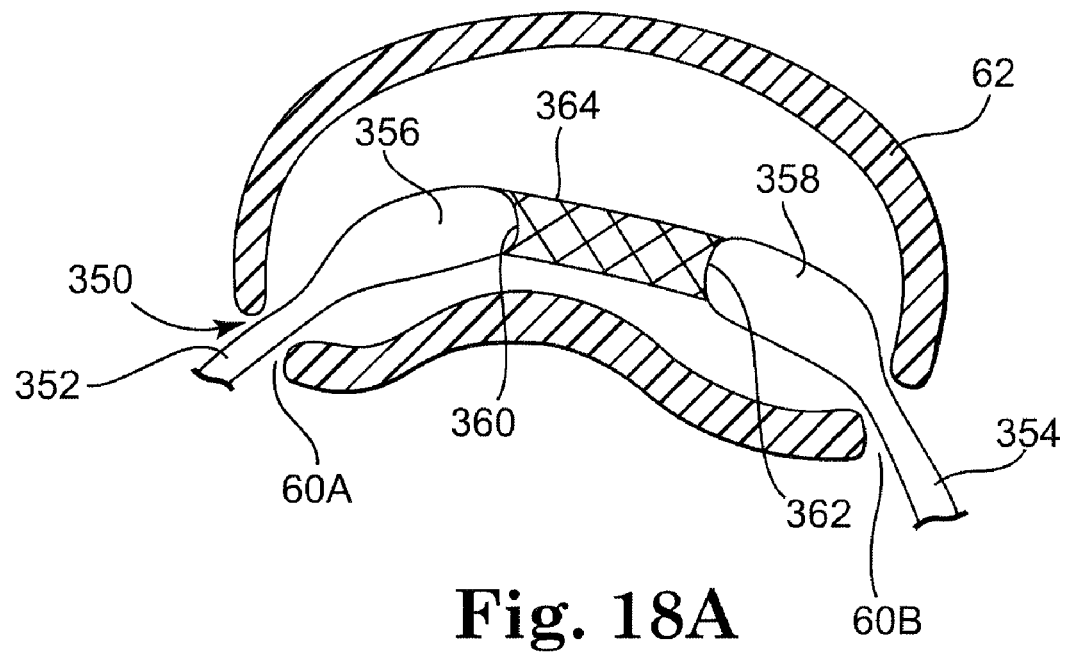
FIGS. 18A and 18B are cross-sectional views of an annulus containing a mold assembly with multiple molds and an alternate pressure activated retention structure in accordance with the present invention.
Figure 18B:
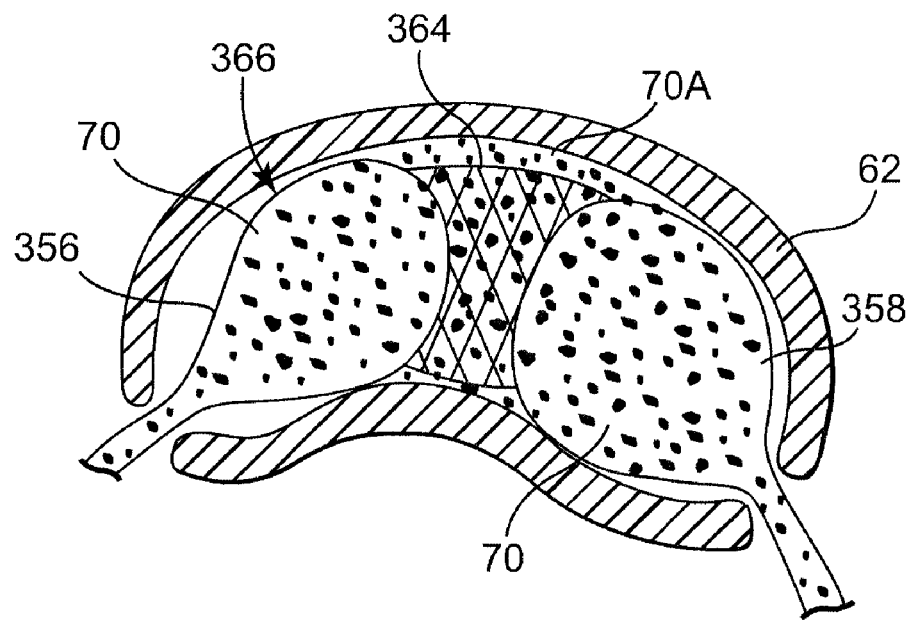

FIGS. 18A and 18B illustrate an alternate mold assembly 350 in accordance with the present invention. Lumens 352, 354 extend into the annulus 62 through different annulotomies 60A, 60B. Lumen 352 is fluidly coupled with mold 356 and lumen 354 is fluidly coupled with mold 358. Reinforcing mesh structure 364 is connected to the molds 356, 358 at locations 360, 362, respectively. As illustrated in FIG. 18B, biomaterial 70 is delivered to the molds 356, 358 causing the retention structure 364 to be compressed and/or stretched within the nuclear cavity 68.

In one embodiment, additional biomaterial 70 can optionally be delivered into the nuclear cavity 68 proximate the retention structure 364. In the illustrated embodiment, the same or a different biomaterial 70A flows around and into the retention structure 364. The biomaterial 70A bonds the retention structure 364 to the annulus 62. The resulting prosthesis 366 has three distinct regions of resiliency. The areas of varying resiliency can be tailored for implants that would be implanted via different surgical approaches, as well as various disease states. The retention structure 364 optionally includes radiopaque properties. A series of images taken during delivery of the biomaterial 70 illustrates the expansion and position of the prosthesis 366 in the nuclear cavity 68.

Figure 18C:
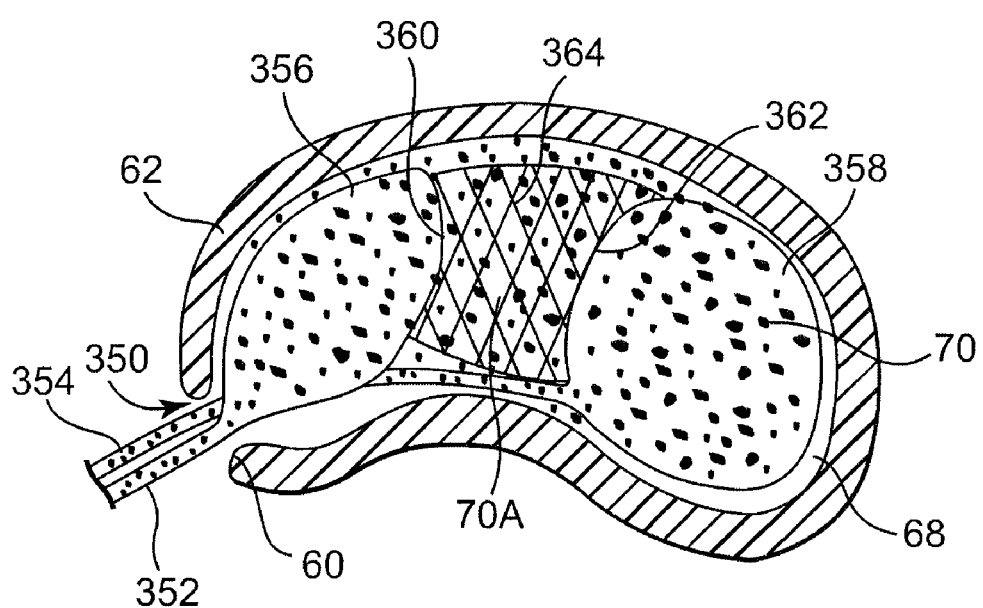
FIG. 18C is a cross-sectional view of the mold assembly of FIGS. 18A and 18B used in a mono-portal application in accordance with the present invention.

FIG. 18C is an alternate configuration of the mold assembly 350 for use with mono-portal applications in accordance with the present invention. Lumens 352, 354 extend into the annulus 62 through a single annulotomy 60. Lumen 352 is fluidly coupled with mold 356 and lumen 354 is fluidly coupled with mold 358. Reinforcing mesh structure 364 is connected to the molds 356, 358 at locations 360, 362, respectively. As illustrated in FIG. 18B, delivery of the biomaterial 70 causing the retention structure 364 to be compressed and/or stretched within the nuclear cavity 68. Additional biomaterial 70A can optionally be delivered into the nuclear cavity 68 proximate the retention structure 364.

FIGS. 19A and 19B are side sectional views of mold assembly 400 in accordance with the present invention. The mold 402 includes a plurality of radiopaque markers 404. In the illustrated embodiment, the radiopaque markers 404 are arranged in a predetermined pattern around the perimeter of the mold 402. As best illustrated in FIG. 19B, once the mold 402 is inflated with the biomaterial, the spacing 406 between the adjacent radiopaque markers 404 increases. By imaging the intervertebral disc space 138 before, during and after delivery of the biomaterial 70, a series of images can be generated showing the change in the spacing between the radiopaque markers 404. Because the spacing between the radiopaque markers 404 is known prior to delivery of the biomaterial, it is possible to calculate the shape and position of the prosthesis 408 illustrated in FIG. 19B using conventional imaging procedures.

FIGS. 20A and 20B illustrate an alternate mold assembly 420 in accordance with the present invention. Mold 422 includes a plurality of radiopaque strips 424 located strategically around its perimeter. When the mold 422 is inflated with biomaterial, the spacing 426 between the radiopaque strips 424 changes, providing an easily imagable indication of the shape and position of the prosthesis 428 in the intervertebral disc space 138.

Figure 21:
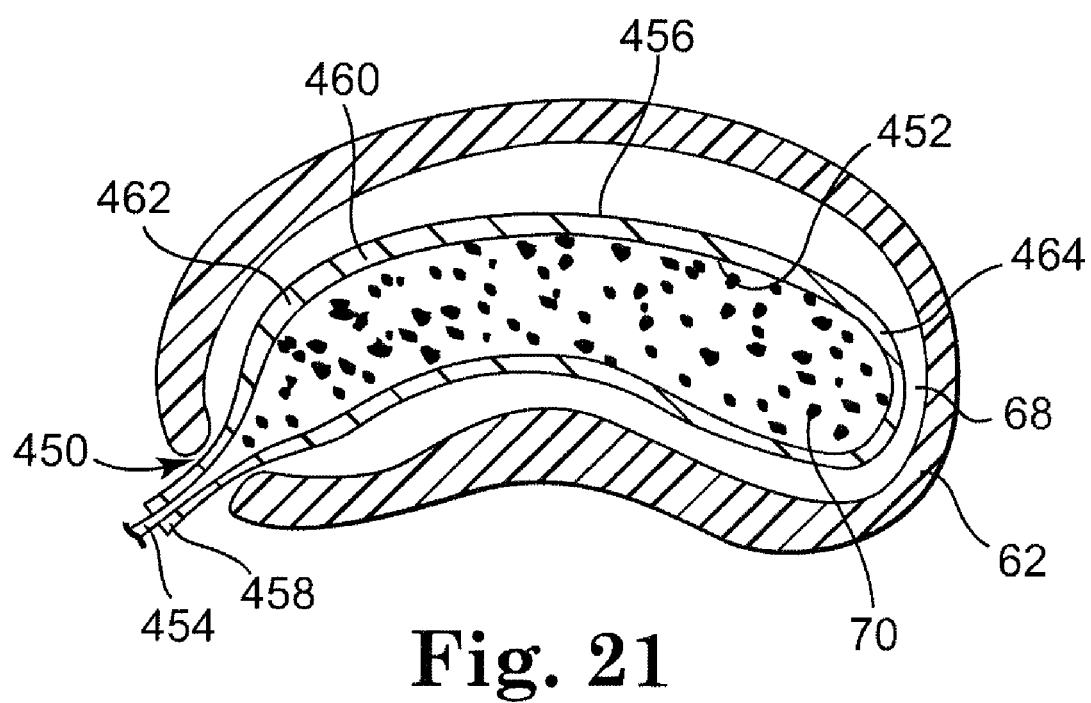
FIG. 21 is a cross-sectional view of an annulus containing a pair of nested molds in accordance with the present invention.

FIG. 21 illustrates an alternate mold assembly 450 in accordance with the present invention. Inner mold 452 is fluidly coupled to lumen 454. Outer mold 456 is fluidly coupled to lumen 458. Biomaterial is delivered through the lumen 454 into the inner mold 452. A radiopaque fluid is preferably delivered to the space 460 between the inner mold 452 and the outer mold 456.

In one embodiment, as the biomaterial 70 is delivered to the inner mold 452, the radiopaque material 462 located in the space 460 is expelled from the nuclear cavity 68 through the lumen 458. A series of images of the annulus 62 will show the progress of the biomaterial 70 expanding the inner mold 452 within the nuclear cavity 68 and the flow of the radiopaque fluid 462 out of the space 460 through the lumen 458.

In another embodiment, once the delivery of the biomaterial 70 is substantially completed and the radiopaque material 462 is expelled from the space 460, a biological material or bioactive agent is injected into the space 460 through the delivery lumen 458. In one embodiment, the outer mold 456 is sufficiently porous to permit the bioactive agent to be expelled into the annular cavity 68, preferably over a period of time. One of the molds 452, 456 optionally includes radiopaque properties. The mold 456 is preferably biodegradable or bioresorbable with a half life greater than the time required to expel the bioactive agents.

In another embodiment, one or more retention structures 464, such as disclosed herein, is located in the space 460 between the inner and outer molds 452, 456. For example, the retention structure 464 may be a woven or non-woven mesh impregnated with the bioactive agent. In another embodiment, the retention structure 464 and the outer mold 456 are a single structure, such as a reinforcing mesh impregnated with the bioactive agent. In yet another embodiment, the outer mold 456 may be a stent-like structure, preferably coated with one or more bioactive agents.

Figure 22:
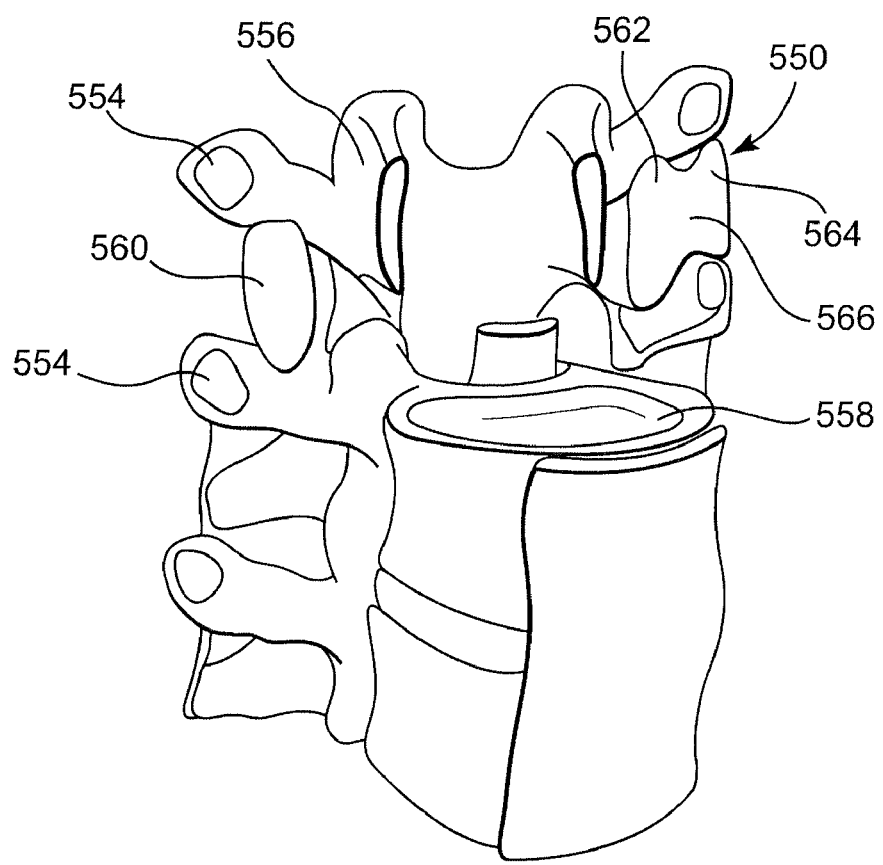
FIG. 22 is a perspective view of the present mold assembly separating adjacent transverse processes in accordance with the present invention.
Figure 23:
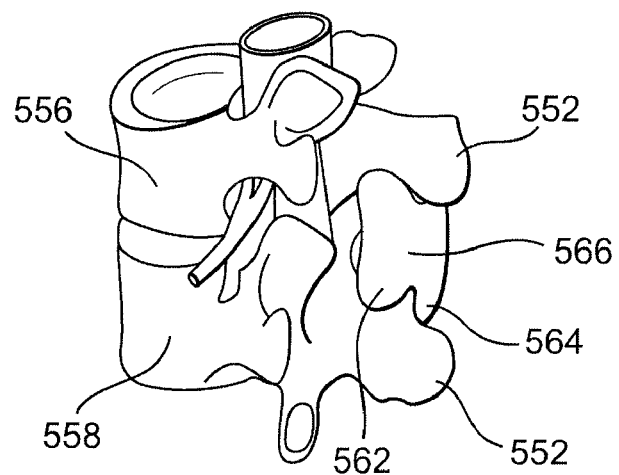
FIG. 23 is a perspective view of the present mold assembly separating adjacent spinous processes in accordance with the present invention.

FIGS. 22 and 23 illustrate use of a mold assembly 550 to maintain the separation between spinous process 552 and/or transverse processes 554 on adjacent vertebrae 556, 558 in according with the present method and apparatus. The mold assembly 550 may be used alone or in combination with an intervertebral mold assembly, such as discussed herein. The mold assembly 550 can also be used to separate the superior articulating process and inferior articulating process, more commonly referred to as the facet joint, on adjacent vertebrae.

In the illustrated embodiment, the mold 560 preferable includes extension 562, 564 that couple or engage with the spinous process or transverse processes 552, 554. Center portion 566 acts as a spacer to maintain the desired separation. In one embodiment, the mold assembly has an H-shaped or figure-8 shaped cross section to facilitate coupling with the various facets on the adjacent vertebral bodies. Attachment of the molds 550 or 560 to the spinous or transverse processes may be further facilitated using sutures, cables, ties, rivets, screws, clamps, sleeves, collars, adhesives, or the like. Any of the mold assemblies and retention structures disclosed herein can be used with the mold assembly 550.

Any of the features disclosed herein can be combined with each other and/or with features disclosed in commonly assigned U.S. patent application Ser. No. 11/268,786, entitled Multi-Lumen Mold for Intervertebral Prosthesis and Method of Using Same, filed Nov. 8, 2005, which is hereby incorporated by reference. Any of the molds and/or lumens disclosed herein can optionally be constructed from biodegradable or bioresorbable materials. The lumens disclosed herein can be constructed from a rigid, semi-rigid, or pliable high tensile strength material. The various components of the mold assemblies disclosed herein may be attached using a variety of techniques, such as adhesives, solvent bonding, mechanical deformation, mechanical interlock, or a variety of other techniques.

The mold assembly of the present invention is preferably inserted into the nuclear cavity 68 through a catheter, such as illustrated in commonly assigned U.S. patent application Ser. No. 11/268,876 entitled Catheter Holder for Spinal Implants, filed Nov. 8, 2005, which is hereby incorporated by reference.

Various methods of performing the nuclectomy are disclosed in commonly assigned U.S. patent Ser. No. 11/304,053 entitled Total Nucleus Replacement Method, filed on Dec. 15, 2005, which is incorporated by reference. Disclosure related to evaluating the nuclectomy or the annulus and delivering the biomaterial 70 are found in commonly assigned U.S. patent application Ser. No. 10/984,493, entitled Multi-Stage Biomaterial Injection System for Spinal Implants, filed Nov. 9, 2004, which is incorporated by reference. Various implant procedures and biomaterials related to intervertebral disc replacement suitable for use with the present multi-lumen mold are disclosed in U.S. Pat. No. 5,556,429 (Felt); U.S. Pat. No. 6,306,177 (Felt, et al.); U.S. Pat. No. 6,248,131 (Felt, et al.); U.S. Pat. No. 5,795,353 (Felt); U.S. Pat. No. 6,079,868 (Rydell); U.S. Pat. No. 6,443,988 (Felt, et al.); U.S. Pat. No. 6,140,452 (Felt, et al.); U.S. Pat. No. 5,888,220 (Felt, et al.); U.S. Pat. No. 6,224,630 (Bao, et al.), and U.S. patent application Ser. Nos. 10/365,868 and 10/365,842, all of which are hereby incorporated by reference. The present mold assemblies can also be used with the method of implanting a prosthetic nucleus disclosed in a commonly assigned U.S. patent application Ser. No. 11/268,856, entitled Lordosis Creating Nucleus Replacement Method and Apparatus, filed on Nov. 8, 2005, which are incorporated herein by reference.

The mold assemblies and methods of the present invention can also be used to repair other joints within the spine such as the facet joints, as well as other joints of the body, including diarthroidal and amphiarthroidal joints. Examples of suitable diarthroidal joints include the ginglymus (a hinge joint, as in the interphalangeal joints and the joint between the humerus and the ulna); throchoides (a pivot joint, as in superior radio-ulnar articulation and atlanto-axial joint); condyloid (ovoid head with elliptical cavity, as in the wrist joint); reciprocal reception (saddle joint formed of convex and concave surfaces, as in the carpo-metacarpal joint of the thumb); enarthrosis (ball and socket joint, as in the hip and shoulder joints) and arthrodia (gliding joint, as in the carpal and tarsal articulations).

The present mold apparatus can also be used for a variety of other procedures, including those listed above. The present mold assembly can also be used to modify the interspinous or transverse process space. The mold can operate as a spacer/distractor between the inferior and superior spinous processes, thus creating a local distraction and kyphosis of wanted. The theory behind these implants is that they expand the intervertebral foramen and thereby relieve pressure on the nerve root and spinal cord. The present injectable prosthesis is adapted to the individual anatomy and clinical situation of the patient, without the need for multiple implant sizes.

Patents and patent applications disclosed herein, including those cited in the Background of the Invention, are hereby incorporated by reference. Other embodiments of the invention are possible. Many of the features of the various embodiments can be combined with features from other embodiments. For example, any of the securing mechanisms disclosed herein can be combined with any of the multi-lumen molds. It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. An assembly for the in situ formation of a prosthesis in an intervertebral disc space between adjacent vertebrae of a patient, the assembly comprising:
   a plurality of retention structures adapted to be delivered sequentially through a lumen into the intervertebral disc space;
   at least a first lumen adapted to be extended into the intervertebral disc space and having a distal end proximate the at least one retention structure;
   one or more in situ curable biomaterials adapted to be delivered to the intervertebral disc space through the first lumen and into engagement with the retention structure, the biomaterial flowing into and around the retention structure, the retention structure adapted to retain at least a portion of the biomaterial in the intervertebral disc space, wherein the retention structure and the curable biomaterial are adapted to be retained in at least a portion of an anatomical annulus without a mold, wherein the at least partially cured biomaterial substantially encapsulates the at least one retention structure and cooperates with the at least one retention structure to comprise the prosthesis; and
   wherein the prosthesis is configured as a motion preservation device.

2. The assembly of claim 1 wherein the retention structure comprises a generally planar structure with openings opposite end plates of the adjacent vertebrae.

3. The assembly of claim 1 wherein the retention structure comprises one or more collapsed retention structures adapted to expand when located in the intervertebral disc space.

4. The assembly of claim 1 wherein the retention structure comprises one or more collapsed retention structures adapted to expand during delivery of the curable biomaterial.

5. The assembly of claim 1 wherein the retention structure comprises an expandable or reorientable retention structure.

6. The assembly of claim 1 wherein the retention structure is adapted to be assembled within the intervertebral disc space.

7. The assembly of claim 1 wherein the retention structure comprises a plurality of interlocking members.

8. The assembly of claim 1 wherein the retention structure comprises one or more inflatable members.

9. The assembly of claim 1 wherein the retention structure comprises a plurality of members adapted to provide resistance to both tensile and compressive forces.

10. The assembly of claim 1 wherein the retention structure comprises a woven or a non-woven member.

11. The assembly of claim 1 wherein the retention structure comprises one or more coiled or kinked members.

12. The assembly of claim 1 wherein the retention structure comprises a plurality of magnetic members.

13. The assembly of claim 1 wherein the retention structure comprise one or more of individual strands, coils, woven or non-woven webs, open cell foams, closed cell foams, combination of open and closed cell foams, scaffolds, cotton-ball fiber matrix, or a generally honeycomb retention structure.

14. The assembly of claim 1 wherein the retention structure comprises:
 a plurality of interconnected cavities; and
 fluid flow devices interposed between at least some of the interconnected cavities, the fluid flow devices selectively controlling the flow of biomaterial into at least some of the cavities.

15. The assembly of claim 1 wherein the retention structure comprises a plurality of discrete cavities at least a portion of which are at least partially filled with biomaterial.

16. The assembly of claim 1 wherein the lumen is coupled to at least one retention structure.

17. The assembly of claim 1 wherein the retention structure comprises a mesh.

18. The assembly of claim 1 wherein the retention structure comprises an expandable mesh.

19. The assembly of claim 1 wherein the retention structure when in the intervertebral disc space comprises at least one cross-sectional area greater than a cross-sectional area of an opening in the first lumen.

20. The assembly of claim 1 wherein the lumen is releasably attached to the retention structure.

21. The assembly of claim 1 comprising at least one valve adapted to retain the biomaterial in the cavity after the lumen is removed.

22. The assembly of claim 1 wherein one or more of the retention structure or the biomaterial comprises a bioactive agent.

23. The assembly of claim 1 wherein delivery of the biomaterial positions the retention structure relative to the intervertebral disc space.

24. The assembly of claim 1 wherein the prosthesis comprises one of a nucleus replacement device, a partial nucleus replacement device, or a total disc replacement device.

25. The assembly of claim 1 wherein the retention structures is adapted to be delivered using minimally invasive techniques.

26. The assembly of claim 1 comprising a mold containing the retention structure and the curable biomaterial.

27. The assembly of claim 1 wherein the distal end of the first lumen is engaged with the retention structure.

28. An assembly for in situ formation of a prosthesis in an intervertebral disc space between adjacent vertebrae of a patient, the assembly comprising:
 a plurality of retention structures adapted to be delivered sequentially through a lumen into the intervertebral disc space, the retention structures filling less than the entire intervertebral disc space;
 at least a first lumen having a distal end fluidly coupled to the retention structures;
 one or more in situ curable biomaterials adapted to be delivered to the intervertebral disc space through the first lumen, the biomaterial flowing into and around the retention structure, the retention structures adapted to retain at least a portion of the biomaterial in the intervertebral disc space, wherein the retention structures and the curable biomaterial are adapted to be retained in at least a portion of an anatomical annulus without a mold, wherein an at least partially cured biomaterial substantially cooperates with the retention structures to comprise the prosthesis; and
 wherein the prosthesis is configured as a motion preservation device.

* * * * *